(12) United States Patent
Bardosh et al.

(10) Patent No.: US 10,433,543 B2
(45) Date of Patent: Oct. 8, 2019

(54) BIOACTIVE BIOPOLYMER FILMS AND COATINGS

(71) Applicant: TerraVerdae BioWorks Inc., Baie d'Urfe (CA)

(72) Inventors: William Bardosh, Beverly, MA (US); Ryan Richard McKenzie, Edmonton (CA); Tizazu Mekonnen, Calgary (CA); Manoj Gokul Nerkar, Edmonton (CA); Misha Miazga-Rodriguez, Edmonton (CA)

(73) Assignee: TerraVerdae BioWorks Inc., Baie d'Urfe, Quebec (CA)

( * ) Notice: Subject to any disclaimer, the term of this patent is extended or adjusted under 35 U.S.C. 154(b) by 348 days.

(21) Appl. No.: 15/487,837

(22) Filed: Apr. 14, 2017

(65) Prior Publication Data

US 2017/0245494 A1 Aug. 31, 2017

Related U.S. Application Data

(63) Continuation-in-part of application No. PCT/CA2015/051035, filed on Oct. 14, 2015, and a continuation-in-part of application No. PCT/CA2015/051036, filed on Oct. 14, 2015.

(60) Provisional application No. 62/208,356, filed on Aug. 21, 2015, provisional application No. 62/122,231, (Continued)

(51) Int. Cl.
| | | |
|---|---|---|
| *A01N 25/34* | (2006.01) | |
| *A01G 13/02* | (2006.01) | |
| *A01G 9/14* | (2006.01) | |
| *C08J 5/18* | (2006.01) | |
| *A01N 25/00* | (2006.01) | |
| *A01N 25/10* | (2006.01) | |
| *A01C 1/06* | (2006.01) | |

(52) U.S. Cl.
CPC .......... *A01N 25/34* (2013.01); *A01G 9/1438* (2013.01); *A01N 25/00* (2013.01); *A01N 25/10* (2013.01); *C08J 5/18* (2013.01); *A01C 1/06* (2013.01); *C08J 2367/04* (2013.01); *Y02A 40/229* (2018.01); *Y02A 40/252* (2018.01); *Y02P 60/218* (2015.11)

(58) Field of Classification Search
CPC ...... A01N 25/34; A01G 9/1438; A01G 13/02; A01G 13/0268; A01G 13/0275
See application file for complete search history.

(56) References Cited

U.S. PATENT DOCUMENTS

| | | | | |
|---|---|---|---|---|
| 10,239,292 | B2 * | 3/2019 | Nissenbaum | B65D 65/46 |
| 2002/0143136 | A1 * | 10/2002 | Noda | B32B 27/20 |
| | | | | 528/272 |
| 2012/0097602 | A1 * | 4/2012 | Tedford | B65D 65/466 |
| | | | | 210/500.1 |

* cited by examiner

*Primary Examiner* — Monica L Williams
(74) *Attorney, Agent, or Firm* — Klarquist Sparkman, LLP

(57) ABSTRACT

A multi-layer bioactive and biodegradable film. The multi-layer film includes one or more bioactive compounds or microorganisms for promoting growth and health of a plant, the bioactive compounds or microorganisms contained between layers of the film, wherein each one of the layers comprises about 60% to about 75% (m/m) polyhydroxyalkanoate. The bioactive compounds or microorganisms may include any one of or a combination of: a metabolite, an anti-microbial compound, an enzyme, a live microorganism, a fertilizer, a plant growth hormone, a preservative, a pesticide or an herbicide. Release of one or more bioactive compounds may be achieved in a timed and controlled manner.

20 Claims, 4 Drawing Sheets

Related U.S. Application Data filed on Oct. 15, 2014, provisional application No. 62/122,245, filed on Oct. 15, 2014.

BIOACTIVE BIOPOLYMER FILMS AND COATINGS

CROSS-REFERENCE TO RELATED APPLICATIONS

This application is (1) a continuation-in-part of International Application No. PCT/CA2015/051035 filed on Oct. 14, 2015, which claims priority to U.S. Provisional Patent Application No. 62/122,245 filed on Oct. 15, 2014 and claims priority to U.S. Provisional Patent Application No. 62/208,386 filed on Aug. 21, 2015; and (2) a continuation-in-part of International Application No. PCT/CA2015/051036 filed on Oct. 14, 2015, which claims priority to U.S. Provisional Patent Application No. 62/122,231 filed on Oct. 15, 2014, the entire disclosures of which are each incorporated herein by reference.

FIELD OF THE INVENTION

The invention relates to the technical field of plastic materials. More specifically, the present invention is in the field of plastic films and coatings.

BACKGROUND OF THE INVENTION

Plastic films and coatings are used for a wide variety of purposes. Examples of potential uses for plastic films and coatings include food packaging, as liners for the packaging of industrial products, shopping and garbage bags, agricultural films, construction films, photographic films, x-ray films and magnetic audio and video recording films.

Plasticulture, defined as the use of plastic materials for agricultural applications, is a well-known technology in agriculture that has a very long history. There are many examples of plasticulture applications, such as silage bags/wraps, greenhouse films and plastic mulches. Plastic mulch has been widely adopted by farmers around the world as a tool for improving crop yield and quality. In 2013, the Grandview Research consultancy projected that the mulch film segment accounted for 44.3% of the market volume from the $5.9 billion agricultural film market, which is expected to continue growing through 2020 at 7.8% per year.

Silage (bale) wrap films are a common application for film materials in an agricultural context. Silage films are typically ductile and adhesive films that are used to tightly wrap bales of fresh or wilting grass. Forage is typically baled with a fixed-chambered baler into uniformly sized bales, which may be either wrapped with silage film using a bale wrapping machine or inserted into a silage bag. The practice of ensiling forage with plastic is particularly common in the dairy industry, which make use of this practice as a cost-effective option for storing high quality feed for cattle. Silage wrap functions to preserve forage materials in the period between when forage is cut and when it is being used as animal fodder. In practice, the plastic materials used to wrap silage preferably have excellent moisture and oxygen barrier properties. Sealing silage with a plastic film creates an anaerobic environment, which encourages anaerobic acid fermentation conditions that result in the decomposition of complex carbohydrates in forage into simpler sugars that are more digestible by animals.

Another common example for the use of plastic films in agriculture is plastic mulching. Agricultural plastic mulch film is typically a sheet of plastic the width of a planting row, plus an additional width on each side of the row onto which soil is piled to hold the sheet in place. In use, the sheet is rolled out for the entire length of the plant row after which holes are punched into it along the length at intervals suitable for the expected crop. Plastic mulch films are widely used around the world because they protect soil from weeds and pests, help to regulate moisture retention by reducing evaporative losses from soil and reduce fertilizer leaching. Plastic mulch films are particularly effective as weed management tools, limiting weed growth by forming a physical barrier above the soil and by blocking sunlight from reaching growing weeds. Plastic mulch is also an important tool for limiting losses due to drought, helping crops to survive drought stress by limiting evaporative water loss from soils and by blocking the growth of weeds that otherwise would draw moisture away from the target crop. Yield losses due to drought stress are increasing due to climate change and intensive agricultural practices that are leading to soil degradation, which is a driver for the increased use of plastic mulches.

Mulch films, silage wraps and silage bags are usually made from either linear low density or high density polyethylene or polypropylene. These types of plastics are extremely strong and flexible, having very long chain polymerized molecules. Under the effect of the energy supplied by UV light or elevated temperatures, these long chains can be degraded over time. Silage films and bags are typically available in a range of colors, with black, blue and green films particularly common. The incorporation of a black colorant, typically carbon black, in silage films and silage bags limits UV degradation. Increased radial heating of black plastic is potentially desirable in northern climates, as it potentially improves silage fermentation conditions and also helps prevent freezing of silage, which facilitates feeding out during the winter. Mulch films are available in a wider range of colors, with black, white, silver, red, blue, brown, green and yellow films commonly available. The opacity of the film governs the amount of radiation available to heat the soil and the growth of weeds under the film. Different colors produce specific soil and ambient temperature conditions under the film and have specific beneficial and detrimental effects on the growth of a particular crop.

Plastic mulches are typically produced from non-biodegradable olefins such as polyethylene or polypropylene, and are generally considered acceptable for organic agriculture under organic standards as long as they are not incorporated into the soil or disposed of in an environmentally-unfriendly manner. However, a significant drawback to typical synthetic plastic mulches is that they have to be removed after they are used, which is a laborious process, while disposal costs are a significant expense for growers.

Oxo-biodegradable mulch films do not meet international standards for biodegradability and compostability and are not true bioplastics. Oxo-biodegradable films are also unacceptable under any standards for organic agriculture. As they are not biosourced and do not meet standards for biodegradability and compostability, they are not accepted as biosourced biodegradable plastic mulches. Conversely, although they can be considered synthetic plastic mulches, organic standards require that synthetic mulches are removed after the growing season and disposed of in an environmentally benign manner. Microplastic fragments are known to persist in the environment at high levels and can be ingested and incorporated into the bodies and tissues of many organisms, where they can cause harm. Oxo-biodegradable films perpetuate, rather than solve, a significant environmental problem.

Various methods have been devised to produce an agricultural mulch film material that degrades in the soil. U.S. Pat. No. 3,454,510 to Newland et al. (incorporated herein by reference in its entirety) describes a degradable mulch film that is produced by blending a pro-oxidant into a water-soluble polyolefin film, resulting in what is generally referred to as an oxo-biodegradable plastic. Among the pro-oxidants that are disclosed are certain metal acetyl acetonates, metal alkyl benzoylacetates, metal acetyl acetonates, metal stearates and metal oleates. Refinements of this process have been developed, such as a film composition described by Cole et al. (U.S. Pat. No. 3,707,056, incorporated herein by reference in its entirety) wherein petroleum coke is incorporated into the mulch film and released as the film degrades to improve the cation exchange capacity of the soil, furnish nutrients and improve soil quality. The pro-oxidant additives added to oxo-biodegradable plastics cause the plastics to fragment after sunlight or heat exposure. While fragmentation makes plastics more readily biodegradable by microorganisms, the biodegradation process still takes months to decades. These films do not meet international standards for compostability such as ASTM D6400, which requires that 60% conversion of the plastic's carbon is reduced to carbon dioxide within 6 months.

Starch has been used as a base material for producing biodegradable mulch films because starch is inexpensive and abundant and can form a film structure. While starch is a natural polymer, a problem with biodegradable film products that are based on starch blends is their typical inclusion of synthetic petroleum-derived polymers, such as polycaprolactone, within the polymer matrix, which prohibits their use in certified organic production unless the film material is manually removed from the soil at the end of the growing season. Starch-based films typically must be coated or blended with water-resistant polymers because starch films otherwise lose strength if they become saturated with water. For example, U.S. Pat. No. 3,949,145 to Otey (incorporated herein by reference in entirety), describes a mulch film formulation including starch and a synthetic polyvinyl alcohol that is coated with a water-resistant coating composed of polyol-toluene-diisocyanate prepolymer and 1 part of poly(vinylidene chloride-acrylonitrile) copolymer or 1 part of poly(vinyl chloride) resin containing a plasticizing amount of a suitable plasticizer.

U.S. Pat. No. 5,292,782 to Bastioli (incorporated herein by reference in entirety), describes a thermoplastic copolymer of starch and a synthetic thermoplastic polymer, such as polycaprolactone, which can be used to produce a biodegradable mulch film.

Polyhydroxyalkanoates are biologically degradable polymers which can be accumulated by microorganisms as sources of carbon and energy. Poly(3-hydroxybutyrate) (PHB) and the copolymer poly(3-hydroxybutyrate)-co-valerate (PHB/HV) are the most known and best studied forms of polyhydroxyalkanoates and are classified as short-chain-length polyhydroxyalkanoates. However, polyhydroxyalkanoates represent a large class of polymers with over 300 variants.

Various methods have been described for producing films and coatings based on polyhydroxyalkanoates. For example, Waddington (U.S. Pat. No. 5,578,382) and Eggink and Northolt (U.S. Pat. No. 5,958,480), each incorporated herein by reference in entirety, describe methods for producing a biodegradable film from polyhydroxyalkanoates, while Bond and Noda (U.S. Pat. No. 7,077,994, incorporated herein by reference in entirety) disclose a method for producing a film from a blend of polyhydroxyalkanoates and starch. U.S. Pat. No. 6,828,357, incorporated herein by reference in entirety, describes a method for creating porous polyhydroxyalkanoates that have a wider range of biodegradation rates, which makes them more suitable in particular for producing a mulch film.

Various methods have been devised to integrate other compounds into plastic films and coatings that are released through a slow or controlled manner. Byron (U.S. Pat. No. 2,169,055, incorporated herein by reference in entirety) describes a mixture of essential oils in cellulose acetate that could be used to form a fragrance emitting film, while Seiner (U.S. Pat. No. 3,655,129, incorporated herein by reference in entirety) describes the entrapment of minute droplets of volatilizable fragrance oil within a polymeric matrix. Funk and Wang (U.S. Pat. No. 8,759,279, incorporated herein by reference in entirety) describe a method for injecting a fragrance into an extruder and blending it with a starch film. Dobo et al. (U.S. Pat. No. 4,267,138, incorporated herein by reference in entirety) describe a coating that slowly releases biologically active compositions such as pharmaceuticals, while Guo and Martin (U.S. Pat. No. 8,680,228, incorporated herein by reference in entirety) disclose a method for producing polyhydroxyalkanoate polymers capable of controlled release of bioactive agents.

A method for producing a degradable agricultural film that releases plant nutrients in a controlled manner was described by Lahalih et al. (U.S. Pat. No. 4,845,888, incorporated herein by reference in entirety). This method for produces a multi-layer film that releases nutrients to the soil. The first layer of the film is formed from a water-soluble synthetic resin such as polyvinyl alcohol, a releasable form of nitrogen and a releasable form of a plant nutrient in addition to nitrogen. A second layer includes a water-soluble synthetic resin having an average molecular weight which is greater than the average molecular weight of the water-soluble synthetic resin in the first layer, such as polyvinyl acetate, and a releasable form of nitrogen admixed therein. The second layer also includes a thin film of water-resistant polymer to retard the degradation rate of the second layer and to slow the release of nitrogen in the second layer. Dujardin et al. (PCT Publication No. WO/2013/143968 and U.S. Pat. No. 8,372,418) describe a multi-layer polyethylene film that releases a pesticide into the soil through diffusion when used as a mulch film. The agricultural films produced as taught by this method are not biodegradable or compostable.

U.S. Patent Publication No. 20120077254, incorporated herein by reference in entirety), describes the use of spent polyhydroxyalkanoate films or shredded polyhydroxyalkanoate films as substrates for anaerobic digestion. The biogas formed through the anaerobic digestion process may be used for electricity generation, as a fuel for heating, cooking or other purposes, or as a feedstock for polyhydroxyalkanoate production by methane-consuming 01 microorganisms, as described in (U.S. Patent Publication No. 20130071890, incorporated herein by reference in entirety).

Legal et al. (U.S. Pat. No. 3,316,676, incorporated herein by reference in entirety) describe an example of a seed coating method in which vermiculite is mixed with a binder such as polyvinyl acetate. After embedding a seed into this mixture, it is compressed to form a pellet. Alternative approaches have been described by Graves (U.S. Pat. No. 3,707,807, incorporated herein by reference in entirety), who describes a seed coating composition that comprises an aqueous emulsion of a water-soluble neutralized copolymer of an $\alpha,\beta$-unsaturated monocarboxylic acid and a lower alkyl acrylate and a crosslinked copolymer of vinyl acetate and a lower alkyl acrylate, while Barke and Luebke (U.S. Pat. No. 4,272,417, incorporated herein by reference in entirety) discloses a seed coating composition comprising a vinyl or alkyl binding agent that is blended into a liquid medium comprising water and a polyol. Danelly (U.S. Pat. No. 4,249,343, incorporated herein by reference in entirety) discloses a water insoluble polymeric microgel that provides protection for the seeds from mechanical and environmental damages and that may be used as a carrier for materials such as fertilizers, herbicides and pesticides.

Useful monomers for the production of microgels that are disclosed by Danelly include acrylic acid; methacrylic acid; hydroxy esters, amino substituted esters and amides of acrylic acid, methacrylic acid and maleic acid; vinylpyridine and derivatives of vinyl pyridine such as 2-methyl-5-vinylpyridine. Obert et al., in U.S. Pat. No. 6,557,298, incorporated herein by reference in entirety, disclose a method for treating a seed with a dry mixture of a hydrogel and an active ingredient. Active ingredients useful for this purpose include pesticides, selective herbicides, chemical hybridizing agents, auxins, antibiotics and other drugs, biological attractants, growth regulators, pheromones, dyes and combinations thereof. The hydrogel and method of application resists loss of coating due to abrasion encountered during handling, storage, transportation, distribution and sowing, and also provides long lasting treatment of the seed with that effect and even, if so desired, provides such treatment to the plant that later emerges from the seed.

U.S. Pat. No. 7,989,391, incorporated herein by reference in entirety discloses a seed coating composition consisting of an aqueous carrier, a pigment colorant, an acrylic latex binder and a fungicide, insecticide, rodenticide, nematocide, miticide or bird repellent, wherein the latex binder is a mixture of methyl methacrylate, styrene, 2-ethylhexyl acrylate, methylol methacrylamide, hydroxyethyl acrylate and methacrylic acid.

U.S. Pat. No. 7,774,978, incorporated herein by reference in entirety, discloses a seed coating with a controlled release rate of an agricultural active ingredient, which is achieved by applying to the seed a film that includes an emulsion of a polymer in a liquid in which both the active ingredient and the polymer have low levels of solubility, and then curing the film to form a water insoluble polymer coating on the surface of the seed.

Encapsulation technologies for intact seeds can also be utilized to improve the propagation of other plants that are difficult or impossible to propagate as seeds by producing synthetic seeds. This approach is particularly common for fruit trees, which are particularly difficult to propagate by planting seeds. One of the problems with fruit trees is that they have a prolonged juvenile phase, which means that breeders must wait for a long time before their crops will produce seeds. Many fruit crops, such as apple trees, are also heterozygotes that are produced by grafting distinct parents to form a hybrid. The seeds produced by these plants have unpredictable variants of their parents' characteristics, and in some cases the seeds that are produced are sterile. Propagation by seed also may be hindered, especially for fruit crops, due to the high dessication-sensitivity of their seeds, minute size, reduced endosperm size, low probability that seeds will germinate, and low tolerance of seeds to long-term storage. Accordingly, Kitto and Janick (Kitto and Janick, 1982, Hort. Sci. 17:448, incorporated herein by reference in entirety) describe a method for producing a synthetic seed by coating a carrot somatic embryo in a mixture of a water-soluble resin, polyoxyethylene glycol (Polyox). Redenbaugh also describes a method for encapsulating somatic embryos in an alginate hydrogel (Redenbaugh, 1984, In Vitro Cell Dev. Biol. Plant. 20:256-257, incorporated herein by reference in entirety). Further development of this technology, and its application to a number of different plant species, is outlined by Rai et al. (Rai et al., 2009, Biotechnology Advances, 27:671-679, incorporated herein by reference in entirety). Noda and Satkowski (WO01094678) describe an application of a polyhydroxyalkanoate copolymer as a coating for agricultural items.

Biostimulants, which are generally defined as formulations of bioactive metabolites and microorganisms that are applied to plants and soils to improve crop vigor, yield, quality and stress tolerance, are a major emerging trend in agriculture, and are increasingly being used by farmers to increase crop health and productivity. The high cost of developing new chemical pesticides, rising insect and weed resistance concerns and growing regulatory and consumer pressure that favors limiting chemicals in the environment are factors that are driving increasing interest in biostimulants. The concept that seed coatings can be used as a delivery system for agricultural chemicals such as fungicides, insecticides, rodenticides, nematocides or miticides is well established. Redenbaugh (U.S. Pat. No. 4,779,376, incorporated herein by reference in entirety), for example, discloses a hydrogel formulation that may be used to encapsulate pesticides, herbicides, insecticides, fungicides, fumigants, repellants, rodenticides, fertilizers, nutrients, sugars, carbohydrates, adenosine triphosphate, microorganisms, growth regulators and hormones around a seed. Various materials may be used to form the gel, such as alginate, carrageenan and locust bean gum.

While past technologies may be effective to a certain degree in providing functionalized biopolymer films and coatings, it remains desirable to provide such films and coatings with enhanced biodegradability and functions to address the various requirements of films and coatings in agriculture and other applications.

Plastic filaments, which are generally defined as threads of plastic, are used to manufacture a wide range of products including, but not limited to, stranded ropes, tooth brush bristles, fabric materials and plastic ties. Plastic filaments are also widely used as feedstocks for three dimensional (3D) printers, and the types of plastics most widely used for this application are typically acrylonitrile butadiene styrene (ABS) and polylactic acid (PLA). ABS is a synthetic copolymer made by polymerizing styrene and acrylonitrile in the presence of butadiene. PLA is a synthetic biopolymer that is typically manufactured from renewable resources such as corn starch and sugar cane.

ABS filaments for 3D printing are generally preferred for printing materials intended to have mechanical uses due to its superior strength, flexibility, machinability and temperature resistance. A significant drawback to ABS is that unpleasant and hazardous odors are produced as it is extruded. It has been shown that ultrafine particulate fumes are produced at a level that is ten times higher when ABS filaments are used in 3D printers than for PLA-based filaments (Stephens et al. 2013. Ultrafine particle emissions from desktop 3D printing. Atmospheric Environment. 79:334-339). PLA filaments are generally available in a wider range of colors and translucencies, which makes them attractive for printing materials intended for display purposes or household uses. However, while PLA meets the ASTM D6400 standard for compostability, which requires that 60% conversion of the plastic's carbon is reduced to carbon dioxide within 6 months, it will only biodegrade quickly if composted in an industrial composting facility configured to heat the material above 60° C. with constant feeding of digestive microbes. PLA does not decompose at an effective rate in simple composting systems.

While past technologies may be effective to a certain degree in providing biodegradable polymer filaments, it remains desirable to provide improved biodegradable polymer filaments with enhanced biodegradability to address the various requirements and improve the safety profile of such filaments.

SUMMARY OF THE INVENTION

The present invention provides bioactive biodegradable polyhydroxyalkanoate-based films and coatings. The films and coatings provide controlled release of biologically active compounds or live microorganisms. These films and coatings may be potentially used for a range of applications as outlined hereinbelow.

One aspect of the present invention is a process for manufacturing a biodegradable bioactive film product, the process comprising:
 a. isolating polyhydroxyalkanoate from a bacterial culture;
 b. bleaching the polyhydroxyalkanoate and dispersing the polyhydroxyalkanoate in a surfactant solution to form a dispersion;
 c. drying the dispersion to obtain dried polyhydroxyalkanoate particles;
 d. mixing the polyhydroxyalkanoate with at least one bioactive compound or organism, at least one nucleating agent, at least one filler, at least one plasticizer and at least one impact modifier or fiber to form a mixture;
 e. extruding the mixture as a film; and
 f. winding the film onto a spool.

In certain embodiments, the polyhydroxyalkanoate is poly(3-hydroxybutyrate), poly(4-hydroxybutyrate) or the copolymer poly(3-hydroxybutyrate)-co-valerate.

In other embodiments the polyhydroxyalkanoate is a medium chain length polyhydroxyalkanoate.

In certain embodiments, drying step is performed by spray-drying.

In certain embodiments, the dried polyhydroxyalkanoate particles are subjected to a cross-linking process before step d).

In certain embodiments, the cross-linking process is effected by addition of a coagent.

In certain embodiments, the bioactive compound or microorganism is a metabolite, an anti-microbial compound, an enzyme, a live microorganism, a fertilizer, a plant growth hormone, a preservative, a pesticide or an herbicide.

In certain embodiments, the controlled release of the bioactive compounds or microorganisms is configured for specific timing to match projected growth stages of a plant.

In certain embodiments, the nucleating agent is talc, mica, boron nitride, crystalline nanocellulose, crystalline microcellulose, sodium benzoate, calcium carbonate, silica, an ionomer, a clay, diacetal, titanium dioxide, dibenzylidene sorbitol, benzophenone, diacetal benzoate, lithium benzoate, sodium benzoate, potassium benzoate, thymine or a sodium organophosphate.

In certain embodiments, the filler is charcoal, a carbon nanotube, a carbon fiber, a steel fiber, graphite, carbon black, algae, cellulose, biochar or clay.

In certain embodiments, the filler conducts electricity or light.

In certain embodiments, the filler includes a filament or dispersed conductive particles dispersed on the polymer.

In certain embodiments, the plasticizer is glycerol, tributyl-O-acetylcitrate, glyceryl triacetate, bis(2-ethylhexyl) adipate, acetyl-tri-n-butyl citrate polyethylene glycol, sorbitol, mannitol or sodium monoleate.

In certain embodiments, wherein the impact modifier or fiber is starch, chitin, polybutylene adipate terephthalate, polybutylene succinate, bio-based polyethylene, natural rubber, polylactic acid, nanocrystalline cellulose, microcrystalline cellulose, lignin, flax, hemp, bamboo or rice husk.

In certain embodiments, step d) further includes mixing a coagent to improve crystallization kinetics, wherein the coagent is triallyl trimesate, N,N-m-phenylenedimaleimide, trimethylopropane triacrylate, 1,2-polybutadiene, neopentylglycol diacrylate, diallyl isophthalate, N-phenylmaleimide or triallyl phosphate.

Another aspect of the invention is a biodegradable bioactive film comprising:
 a. about 60% to about 75% (m/m) polyhydroxyalkanoate;
 b. about 0.01% to about 0.05% (m/m) of a bioactive compound or microorganism;
 c. about 0.2 to about 1% of a nucleating agent;
 d. about 10% to about 40% (m/m) of a plasticizer;
 e. about 0.5% to about 30% (m/m) of a filler; and
 f. about 10% to about 40% (m/m) of an impact modifier or fiber.

In certain embodiments, the bioactive compound or microorganism is a metabolite, an anti-microbial compound, an enzyme, a live microorganism, a fertilizer, a plant growth hormone, a preservative, a pesticide or an herbicide.

In certain embodiments, the nucleating agent is talc, mica, boron nitride, crystalline nanocellulose, crystalline microcellulose, sodium benzoate, calcium carbonate, silica, an ionomer, a clay, diacetal, titanium dioxide, dibenzylidene sorbitol, benzophenone, diacetal benzoate, lithium benzoate, sodium benzoate, potassium benzoate, thymine or a sodium organophosphate.

In certain embodiments, the filler is charcoal, a carbon nanotube, a carbon fiber, a steel fiber, graphite, carbon black, algae, cellulose, biochar or clay.

In certain embodiments, the filler conducts or generates electricity or light.

In certain embodiments, the plasticizer is glycerol, tributyl-O-acetylcitrate, glyceryl triacetate, bis(2-ethylhexyl) adipate, acetyl-tri-n-butyl citrate polyethylene glycol, sorbitol, mannitol and sodium monoleate.

In certain embodiments, the impact modifier or fiber is starch, chitin, polybutylene adipate terephthalate, polybutylene succinate, bio-based polyethylene, natural rubber, polylactic acid, nanocrystalline cellulose, microcrystalline cellulose, lignin, flax, hemp, bamboo or rice husk.

In certain embodiments, the film further comprises a coagent to improve crystallization kinetics, wherein the coagent is triallyl trimesate, N,N-m-phenylenedimaleimide, trimethylopropane triacrylate, 1,2-polybutadiene, neopentylglycol diacrylate, diallyl isophthalate, N-phenylmaleimide or triallyl phosphate.

In certain embodiments, a first bioactive compound of the one or more bioactive compounds is a microorganism located within or adjacent to a first layer of the film, the microorganism capable of metabolizing polyhydroxyalkanoate released from the first layer.

In certain embodiments, the microorganism promotes degradation of a second layer of the film and wherein degradation of the second layer releases a second bioactive compound which enhances plant growth.

In certain embodiments, a first bioactive compound released from at least one of the layers triggers activity of a second bioactive compound from a previously degraded layer.

Another aspect of the present invention is a method for promoting growth of a plant and suppressing growth of weeds, the method comprising covering the plants with the bioactive and biodegradable film as described herein.

Another aspect of the present invention is a method for promoting growth of a tree or plant, the method comprising covering the plants with the bioactive and biodegradable film as described herein, wherein as the film degrades, the bioactive is released promoting plant growth. The bioactive may be a germination factor, a root enhancer, may promote stem growth or elongation, or any other plant growth stimulant.

Another aspect of the present invention is a method for propagating a plant, the method comprising forming a wound on the plant and covering the wound with the bioactive and biodegradable film as described herein, wherein the bioactive compound comprises a plant growth hormone promoting the generation of shoots or roots for use in propagating the plant.

Another aspect of the present invention is method for preserving silage comprising wrapping the silage in the bioactive and biodegradable film as described herein.

Another aspect of the present invention is a method for preventing microbial growth on a surface, the method comprising coating the surface with the bioactive and biodegradable film as described herein, wherein the bioactive compound is an antimicrobial or anti-adhesion compound.

Another aspect of the present invention is a method for promoting growth of a tree or plant, the method comprising covering the plants with the bioactive and biodegradable film as described herein, wherein the film includes a filler that conducts electricity or light, and providing an electric current to the film, thereby promoting the release of the bioactive compound or microorganism.

Another aspect of the present invention is a process for providing seeds with a biodegradable bioactive polymer coating, the method comprising:
  a. isolating polyhydroxyalkanoate from a bacterial culture;
  b. bleaching the polyhydroxyalkanoate and dispersing the polyhydroxyalkanoate in a surfactant solution to form a dispersion;
  c. drying the dispersion to obtain dried polyhydroxyalkanoate particles;
  d. mixing the dried polyhydroxyalkanoate particles with an organic solvent and one or more additives to solubilize the polyhydroxyalkanoate polymer in a mixture;
  e. soaking the seeds in the mixture or spray-coating the seeds with the mixture;
  f. drying the seeds to obtain dried coated seeds; and
  g. applying a bioactive compound or microorganism to the dried coated seeds.

In certain embodiments, the drying step is performed by spray-drying.

In certain embodiments, the dried polyhydroxyalkanoate particles have an average diameter from about 150 to about 250 micrometers.

In certain embodiments, the dried polyhydroxyalkanoate particles are subjected to a cross-linking process before step d).

In certain embodiments, pore porosity of the coating is controlled by controlling solvent evaporation or by contacting the coating with a pore producing agent.

In certain embodiments, the pore producing agent is an anti-solvent for the polyhydroxyalkanoate.

In certain embodiments, the anti-solvent is water.

In certain embodiments, the polyhydroxyalkanoate is a medium-chain length or short-chain length polyhydroxyalkanoate.

In certain embodiments, the solvent is chloroform, dichloromethane, 1,2,2-tetrachloroethane, ethylene carbonate, propylene carbonate, acetic anhydride, N,N-dimethylformamide, ethylacetoacetate, acetic acid, 2,2,2-trifluoroethanol, a higher alcohol having more than three carbon atoms, dioxane, toluene, pyridine, benzene, acetone, tetrahydrofuran, diethyl ether, n-hexane, 2-propanol or xylene.

In certain embodiments, step d) further comprises adding any one of or a combination of any of the following additives to the mixture: starch, pectin, one or more proteins, a plasticizer and an antioxidant.

In certain embodiments, the mixture contains at least 50% (m/m) of polyhydroxyalkanoate.

In certain embodiments, the bioactive compound or microorganism is an insecticide, fertilizer, soil amending microorganism, or a nucleic acid-based inhibitor or modulator of gene expression.

In certain embodiments, the process further comprises repeating at least steps d) to e) with a different mixture to produce at least a second polymer coating layer.

Another aspect of the present invention is a process for providing seeds with a biodegradable bioactive polymer coating, the method comprising:
  a. isolating polyhydroxyalkanoate from a bacterial culture;
  b. bleaching the polyhydroxyalkanoate and dispersing the polyhydroxyalkanoate in a surfactant solution to form a dispersion;
  c. drying the dispersion to obtain dried polyhydroxyalkanoate particles;
  d. preparing a triblock copolymer including polyhydroxyalkanoate;
  e. mixing the dried polyhydroxyalkanoate particles with an α-cyclodextrin to obtain a hydrogel;
  f. mixing the hydrogel with a bioactive compound or microorganism; and
  g. applying the hydrogel to the seeds.

Another aspect of the invention is a multi-layer biodegradable film or coating, comprising one or more bioactive compounds or microorganisms for promoting growth or heath of a plant, the bioactive compounds or microorganisms contained within or between layers of the film, wherein each one of the layers comprises about 60% to about 75% (m/m) polyhydroxyalkanoate.

In some embodiments, the bioactive compounds or microorganisms comprise any one of or a combination of: a metabolite, an anti-microbial or anti-fungal compound, enzyme, a carbohydrate, a nucleic acid, a protein, a live microorganism, a fertilizer, a plant growth hormone, a preservative, a pesticide or an herbicide.

In some embodiments, the plant growth hormone comprises any one of or a combination of a synthetic hormone, an auxin, a gibberellin, a cytokinin, a brassinosteroid, abscisic acid and ethylene.

In some embodiments, at least one layer of the two or more layers has a composition configured to undergo controlled, timed biodegradation at a different rate than the rates of biodegradation of remaining layers of the two or more layers.

In some embodiments, the multi-layer biodegradable film or coating comprises three or more layers of the biodegradable film having at least a first bioactive compound or microorganism in or between a first layer of the biodegradable film and a second layer of the biodegradable film and at least a second bioactive compound or microorganism in or between the second layer of the biodegradable film and a third layer of the biodegradable film or at least a first bioactive compound or organism located in or within one of the three or more layers and at least a second bioactive compound or organism located in or between another of the three or more layers.

In some embodiments, the first bioactive compound is a plant hormone promoting seed germination and the second bioactive compound is a plant hormone which promotes stem elongation, leaf growth, fruiting, injury repair, water uptake or protection against extreme temperatures or wherein the second bioactive compound is an herbicide or an insecticide.

In some embodiments, the first layer has a composition different from the second and third layers, the second layer has a composition different than the first and third layers and the third layer has a composition different than the first and second layers.

In some embodiments, at least one of the three layers of the biodegradable film degrades at a faster rate than the remaining two layers to provide different bioactive compounds for different growth needs.

In some embodiments, degradation of one or more of the layers is initiated by an artificial stimulus or a natural environmental stimulus.

In some embodiments, the artificial stimulus is a change in temperature, administration of an electrical current or irradiation with light.

In some embodiments, the natural environmental stimulus is precipitation, sunlight, pH, nutrient concentration or other natural trigger.

In some embodiments, at least one of the layers comprises about 0.5% to about 30% (m/m) of a filler comprising charcoal, a carbon nanotube, a carbon fiber, a steel fiber, graphene graphite, carbon black, algae, cellulose, nanocrystalline cellulose, biochar clay or any combination thereof.

In some embodiments, the filler conducts electricity and/or light.

In some embodiments, one or more of the bioactive compounds are encased in hydrogel or a thermoprotectant to protect the bioactive compounds against degradation during manufacture.

In some embodiments, a first bioactive compound of the one or more bioactive compounds is a microorganism located within or adjacent to a first layer of the film, the microorganism capable of metabolizing polyhydroxyalkanoate released from the first layer.

In some embodiments, the microorganism promotes degradation of a second layer of the film and wherein degradation of the second layer releases a second bioactive compound which enhances plant growth.

In some embodiments, a first bioactive compound released from at least one of the layers triggers activity of a second bioactive compound from a previously degraded layer.

In some embodiments, at least one of the layers has micro- or nano-pores or channels provided to allow uptake or release of one or more nutrients or one or more additional bioactive compounds, wherein the micro- or nano-pores or channels are activated by environmental conditions and/or biodegradation of the layers to expose the micro- or nano-pores or channels and allow transport of the nutrients or additional bioactive compounds.

Another aspect of the invention is a method for promoting growth of a tree or plant, the method comprising the steps of: at least partially wrapping the tree or plant or covering a seed of the plant with the multi-layer biodegradable film or coating of claim 1, wherein the film includes a filler that conducts electricity and/or light, and providing an electric current and/or light to the film, thereby promoting the release of the bioactive compounds or microorganisms.

In some embodiments, the electricity and/or light breaks down one or more of the layers, thereby allowing the bioactive compounds or microorganisms to be released from the multi-layer film.

Another aspect of the present invention is a process for manufacturing a biodegradable polymer filament product, the process comprising:
  a. isolating polyhydroxyalkanoate from a bacterial culture;
  b. dispersing the polyhydroxyalkanoate in a surfactant solution to form a dispersion;
  c. drying the dispersion to obtain dried polyhydroxyalkanoate particles;
  d. mixing the polyhydroxyalkanoate with a plurality of components including a toughening agent, a plasticizer, a nucleating agent, an antioxidant and an adhesive;
  e. extruding the mixture as a filament; and
  f. winding the filament onto a spool.

Another aspect of the invention is a biodegradable filament for 3D printing, the filament comprising:
  a. about 50% to about 80% (m/m) polyhydroxyalkanoate;
  b. about 10% to about 50% (m/m) of a toughening agent;
  c. about 0.5% to about 30% of a plasticizer;
  d. about 0.1% to about 1% of a nucleating agent;
  e. about 0.1% to about 1% of an antioxidant; and
  f. about 0.01% to about 2% of an adhesive.

In certain embodiments, the filament further comprises about 0.01% to about 1% of a coloring agent.

In certain embodiments, the coloring agent is an organic pigment selected from the group consisting of: alizarin, anthoxanthin, arylide yellow, bilin, bistre, bone char, caput mortuum, carmine, crimson, diarylide pigment, Dragon's blood, Gamboge, Indian yellow, indigo dye, naphthol red, ommochrome, perinone, phthalocyanine Blue BN, phthalocyanine Green G, Pigment Yellow 10, Pigment yellow 139, Pigment Yellow 16, Pigment yellow 185, Pigment Yellow 81, Pigment yellow 83, quinacridone, Rose madder, Rylene dye, sepia ink and Tyrian purple.

In certain embodiments, the filament further comprises about 0.5% to 20% of a filler.

In certain embodiments, the filler conducts electricity or light.

In certain embodiments, the filler is conductive carbon black, a carbon nanotube or a steel fiber.

In certain embodiments, the filler is calcium carbonate, nanocrystalline cellulose, lignin or rice husk.

In certain embodiments, the filament further comprises a phosphorescence compound.

In certain embodiments, the phosphorescence compound is zinc sulfide.

In certain embodiments, the polyhydroxyalkanoate is poly(3-hydroxybutyrate) or the copolymer poly(3-hydroxybutyrate)-co-valerate.

In certain embodiments, the polyhydroxyalkanoate is a medium-chain length polyhydroxyalkanoate.

In certain embodiments, the nucleating agent is talc, mica, boron nitride, crystalline nanocellulose, crystalline microcellulose, sodium benzoate, calcium carbonate, silica, an ionomer, a clay, diacetal, titanium dioxide, dibenzylidene sorbitol, benzophenone, diacetal benzoate, lithium benzoate, sodium benzoate, potassium benzoate, thymine or a sodium organophosphate.

In certain embodiments, the plasticizer is glycerol, tributyl-O-acetylcitrate, glyceryl triacetate, bis(2-ethylhexyl) adipate, acetyl-tri-n-butyl citrate polyethylene glycol, sorbitol, mannitol and sodium monoleate.

In certain embodiments, the strengthening polymer or fiber is starch, chitin, polybutylene adipate terephthalate, polybutylene succinate, bio-based polyethylene, natural rubber, polylactic acid, nanocrystalline cellulose, microcrystalline cellulose, lignin, flax, hemp, bamboo or rice husk.

In certain embodiments, the filament further comprises a coagent to improve crystallization kinetics, wherein the coagent is triallyl trimesate, N,N-m-phenylenedimaleimide, trimethylopropane triacrylate, 1,2-polybutadiene, neopentylglycol diacrylate, diallyl isophthalate, N-phenylmaleimide or triallyl phosphate In certain embodiments, the filament further comprises pentaerythritol tetrakis(3-(3,5-di-tert-butyl-4-hydroxyphenyl)propionate), a hindered amine-containing antioxidant, a hindered phenol-containing antioxidant, a phosphite-containing antioxidant or a sulphur-containing antioxidant.

In certain embodiments, the toughening agent is polybutyrate adipate terephthalate, polybutylene succinate, starch, bio-based polyethylene, natural rubber, polylactic acid, a polyamide, a polyimide, a polycarbonate, a polyolefin, styrene, ethylene, butylene or polyethylene-octene.

In certain embodiments, the adhesive is based on epoxy, polyurethane, silicone, acrylate, polyvinyl acetate, or polyimide.

In certain embodiments, the filament further comprises an outer coating.

In certain embodiments, the coating is paraffin wax, polyvinyl alcohol, ethylene vinyl acetate, polyvinyl acetate, ethylene acrylic acid, ethylene ethyl acrylate, ethylene methacrylate or ethylene methacrylic acid.

BRIEF DESCRIPTION OF THE DRAWINGS

Various objects, features and advantages of the invention will be apparent from the following description of particular embodiments of the invention, as illustrated in the accompanying drawings. The drawings are not necessarily to scale, emphasis instead being placed upon illustrating the principles of various embodiments of the invention. Similar reference numerals indicate similar components.

DETAILED DESCRIPTION OF THE INVENTION

Figure 1:
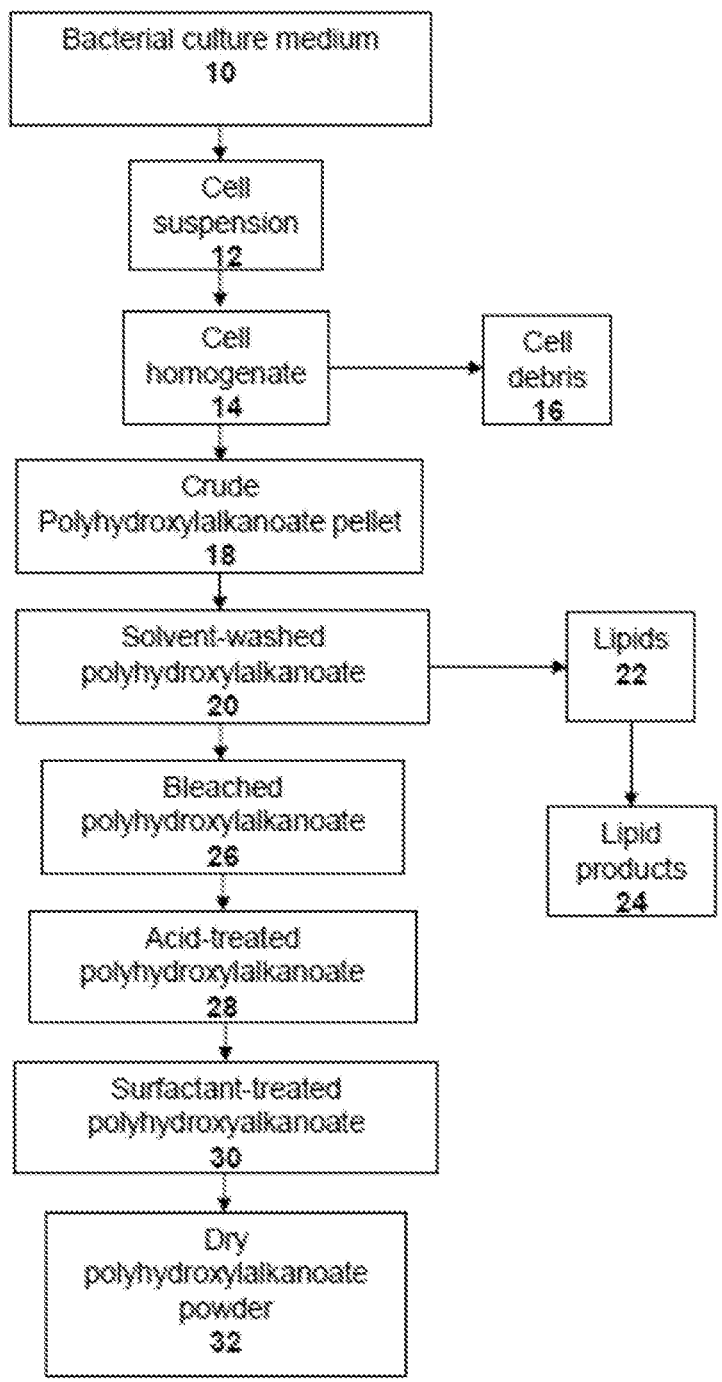
FIG. 1 is a process diagram for purification of polyhydroxyalkanoate from a bacterial culture.

Rationale
  Bioactive Films—
  A major problem with agricultural films is that the plastic partially degrades and the film breaks up into large pieces. Certain weeds can also grow through mulch films or discarded silage films and anchor the films to the ground. This makes lifting difficult and causes the films to break apart. Once removed from the soil, disposing the film is a problem. It is not easy to recycle agricultural films which are heavily contaminated with soils or other debris. In many areas it is not permitted to burn the film. Many landfills will not accept such films as waste and often burying such waste on a farm can cause problems with water flow and soil contamination.

The present inventors have recognized that the solution to these problems is to provide biodegradable agricultural films of a type that can either (1) merely be ploughed into the soil at the end of the season or before the next planting season where they will degrade and disintegrate, thereby becoming a useful component of the soil and removing the chance of any contamination, or, (2) be used as a substrate for on-farm anaerobic digestion to produce a solid, digested material that can be used as a soil conditioner to increase the organic content of soils and as a biogas source that can be used for electrical power generation, as a fuel for vehicles, a cooking fuel or as a substrate for the production of polyhydroxyalkanoates and/or other high-value biochemicals through a closed-loop recycling process.

The biodegradable polyhydroxyalkanoate-based films and coatings of the present invention include bioactive compounds or microorganisms to provide timed, controlled release of the biologically active compounds or microorganisms. These films and coatings are designed for use in a range of applications, including, but not limited to, biodegradable agricultural films for various applications such as silage bales, mulch films and planting pots or other containers.

A known limitation of using homopolymers of polyhydroxyalkanoates, such as poly(3-hydroxybutyrate), or copolymers thereof, such as poly(3-hydroxybutyrate)-co-valerate, is that the material may be too brittle for a number of applications. One solution to these problems is to blend polyhydroxyalkanoate with other additives that modify its properties. In addition, the inventors recognize that a benefit of using polyhydroxyalkanoates is that they are a source of carbon and energy in embodiments where microorganisms are included alone or in combination as a bioactive component in films and coatings, and accordingly using polyhydroxyalkanoates will stimulate the growth of the microorganisms and enhance their survival to maximize benefits provided by their presence. These microorganisms either alone or in combination with bioactive compounds, trigger or promote plant growth and/or plant health.

Biodegradable 3D Printing Filaments—
A drawback that is common to both ABS and PLA is that both polymers must be processed at a relatively high temperature (210-255° C.) due to the higher melting and glass transition temperatures for both polymer types, which increases processing cost. In order to avoid warpage of the plastics, which may be induced due to rapid cooling from these high temperatures, 3D printers generally are required to have a heated bed in order to control the cooling rate, which adds to the cost of manufacturing the 3D printer hardware.

Three dimensional printing can be achieved by techniques such as fused deposition modelling, which use extruded filaments and granular binding methods such as selective laser sintering and selective heat sintering. Presently, polymeric components are typically printed using fused deposition modelling.

In accordance with the invention, embodiments of the filament compositions described herein are used in all three dimensional printing techniques, subject to certain modifications. For example, it is recognized that compositions used in selective laser sintering and selective heat sintering will benefit from pulverization of the polymer composition blend into a fine powder.

Like PLA, polyhydroxyalkanoates are biopolymers. However, polyhydroxyalkanoates also possess a number of properties that may make them more suitable for source material for 3D printing than PLA. Polyhydroxyalkanoates are typically more UV stable than PLA. Polyhydroxyalkanoates also demonstrate lower permeability to water than PLA, while the higher crystallinity of polyhydroxyalkanoates makes them stronger than PLA. Finally, while the melting temperature for both PHA and PLA is similar, and while both materials are classified as biodegradable and compostable, the low glass transition temperature for polyhydroxyalkanoates (2° C. in the case of polyhydroxybutyrate) means that they can be printed at lower temperature.

Definitions

As used herein, the term "plasticizers" (also known as "dispersants") refers to additives that increase the plasticity or fluidity of a material. The dominant applications are for plastics, especially polyvinyl chloride (PVC). The properties of other materials are also improved when blended with plasticizers including concrete, clays, and related products. Plasticizers are common components of films and cables.

The term "Young's modulus," also known as the "tensile modulus" or "elastic modulus," is a measure of the stiffness of an elastic material and is a quantity used to characterize materials. It is defined as the ratio of the stress (force per unit area) along an axis to the strain (ratio of deformation over initial length) along that axis in the range of stress in which Hooke's law holds. Young's modulus is the most common elastic modulus, sometimes called the modulus of elasticity, but there are other elastic moduli such as the bulk modulus and the shear modulus. Young's modulus is the ratio of stress (which has units of pressure) to strain (which is dimensionless), and so Young's modulus has units of pressure. Its SI unit is therefore the Pascal (Pa or $N/m^2$ or $m^{-1} \cdot kg \cdot s^{-2}$). The practical units used are megaPascals (MPa or $N/mm^2$) or gigaPascals (GPa or $kN/mm^2$). In United States customary units, it is expressed as pounds (force) per square inch (psi). The abbreviation ksi refers to "kips per square inch", or thousands of psi. As examples, polypropylene has a Young's modulus of 1.5-2 GPa and diamond has a Young's modulus of 1,050-1210 GPa. Tensile tests measure the force required to break a plastic sample specimen and the extent to which the specimen stretches or elongates to that breaking point. Tensile tests produce stress-strain diagrams used to determine tensile modulus, tensile strength (at yield and at break), tensile strain, elongation and percent elongation at yield, and elongation and percent elongation at break.

As used herein, the term "impact strength" refers to the ability of a material to absorb energy and plastically deform without fracturing. One definition of material impact strength is the amount of energy per unit volume that a material can absorb before rupturing. It is also defined as a material's resistance to fracture when stressed. Impact strength is measured in units of joule per cubic meter ($J \cdot m^{-3}$) in the SI system and inch-pound-force per cubic inch ($in \cdot lbf \cdot in^{-3}$) in US customary units.

As used herein, the term "extrusion" refers to a process for generation of objects of a fixed cross-sectional profile. A material is pushed through a die of the desired cross-section. A polymer extrusion process involves heating to melt the polymer. Typically a single or twin screw system is used to convey molten plastic material through the extruder. Apart from melting and conveying extruder also mixes two or more plastics or other materials. The material exits the extruder at the die and it takes shape of the die. Molten plastics leave the die at temperatures at or above the melting temperature of the material. The object emerging from the extruder is typically passed through a water tank to cool it down before it is cut into pellets or wound upon a spool. Film extrusion is used to extrude plastic films using specific dies. The purpose of the die is to reorient and guide the flow of polymer melt from a single round output from the extruder to a thin, flat planar flow. It provides a constant, uniform flow across the entire cross sectional area of the die. Cooling is typically by pulling through a set of cooling rolls. In film extrusion, these rolls not only deliver the necessary cooling but also determine film thickness and surface texture. Co-extrusion is often used to apply one or more layers on top of a base material to obtain specific properties such as UV-absorption, texture, oxygen permeation resistance, or energy reflection.

As used herein, the term "spray drying" refers to a method of producing a dry powder from a liquid or slurry by rapidly drying with a hot gas. This method is used for drying of many thermally-sensitive materials such as foods and pharmaceuticals. A consistent particle size distribution is a reason for spray drying of industrial products such as catalysts. Air is the heated drying medium; however, if the liquid is a flammable solvent such as ethanol or the product is oxygen-sensitive then nitrogen is used. All spray dryers use some type of atomizer or spray nozzle to disperse the liquid or slurry into a controlled drop size spray. The most common of these are rotary disks and single-fluid high pressure swirl nozzles. Atomizer wheels are known to provide broader particle size distribution, but both methods allow for consistent distribution of particle size. Alternatively, for some applications, two-fluid or ultrasonic nozzles are used. Depending on the process needs, drop sizes from 10 to 500 μm can be achieved with the appropriate choices. The most common applications are in the 100 to 200 μm diameter range. The dry powder is often free-flowing. The most common spray dryers are called "single effect" spray dryers as there is only one stream of drying air at the top of the drying chamber. In most cases the air is blown in co-current of the sprayed liquid. The powders obtained with such type of dryers are fine with a lot of dusts and a poor flowability. In order to reduce dust and increase the flowability of the powders, a new generation of spray dryers known as "multiple effect" spray dryers have been developed. Instead of drying the liquid in one stage, the drying is done in two steps: one at the top (as per single effect) and one for an integrated static bed at the bottom of the chamber. The integration of this fluidized bed allows, by fluidizing the powder inside a humid atmosphere, to agglomerate the fine particles and to obtain granules having commonly a medium particle size within a range of 100 to 300 μm. Because of this large particle size, these powders are free-flowing. The fine powders generated by the first stage drying can be recycled in continuous flow either at the top of the chamber (around the sprayed liquid) or at the bottom inside the integrated fluidized bed. The drying of the powder can be finalized on an external vibrating fluidized bed. The hot drying gas is passed as a co-current or counter-current flow to the atomizer direction. The co-current flow enables the particles to have a lower residence time within the system and the particle separator (typically a cyclone device) operates more efficiently. The counter-current flow method enables a greater residence time of the particles in the chamber and usually is paired with a fluidized bed system. Alternatives to spray dryers include freeze dryers, drum dryers, and pulse combustion dryers.

As used herein, the term "nucleating agent" refers to any agent used to modify the rate of crystallization of a polymer.

As used herein, the term "homopolymer" refers to a polymer chain formed of only one type of monomer, As used herein, the term "copolymer" refers to a polymer chain formed of two different types of monomers joined to each other.

As used herein, the term "biodegradable" and the related term "biodegradability" refer to the susceptibility of a given material to be decomposed by bacteria or other microorganisms. A Micro-Oxymax Respirometer System (Columbus Instruments Inc., Columbus, Ohio, USA) is appropriate for testing of biodegradation of bioactive polyhydroxyalkanoate films. Carbon dioxide evolution from the bioactive films and coatings mixed with compost will be measured using this system. Other systems may also be used to test biodegradability.

As used herein, the term "tree tube" (also known as "treeshelter" and "tree protector" refers to a tube formed of polymeric material which is used to protect a ground-adjacent portion of a tree or plant from insects and animals such as rodents, rabbits, deer, lawnmowers and other hazards. Examples of uses of tree tubes are described, for example, at (http://wilsonforsup.com/products/tree-tubes/, which is incorporated herein by reference).

As used herein, the term "tear strength" refers to a measure of how well a material can withstand the effects of tearing. More specifically however it is how well a material resists the growth of any cuts when under tension. Tear resistance can be measured by the ASTM D412 method (the same used to measure tensile strength, modulus and elongation. The sample is held between two holders and a uniform pulling force is applied until the aforementioned deformation occurs. Tear strength is then calculated by dividing the force applied by the thickness of the material. Universal testing machine is used for to measure tear strength of a material.

As used herein, the terms "electric conductivity" and the related terms "electrically conductive" and "electrically conducting" refer to the ability of a material to conduct an electric current. Electric conductivity of polymer sample can be measured using a standard four point measurement process. The current source is connected to both ends of the sample. The voltmeter leads are placed a known distance apart. The resistivity is calculated from the cross-sectional area of the sample and distance between the voltage leads as follows:

$$\rho = \left(\frac{V}{I}\right) \times \left(\frac{A}{L}\right)$$

where:
$\rho$—Resistivity in $\Omega m$
V—Applied voltage (V)
I—Measured current (A)
A—Cross sectional area of sample (W×t) in $cm^2$
L—Length of distance between voltmeter in cm As used herein, the term "polymer morphology" refers to the arrangement and microscale ordering of polymer chains. Morphology of polymer blends involves measurements of dispersion of a dispersed phase or fillers into a polymer matrix. Blend morphology has a substantial effect on mechanical properties and is an important property of polymer blends and composites. Microscopic techniques such as transition electron microscopy and scanning electron microscopy are used to investigate polymer morphology.

As used herein, the term "medium chain length polyhydroxyalkanoate" refers to a polyhydroxyalkanoate chain having 6 to 14 carbon atoms. As used herein the term "short chain length polyhydroxyalkanoate" refers to a polyhydroxyalkanoate chain having 2 to 5 carbon atoms.

As used herein, the term "filament" refers to a thread-like object or fiber formed of a blend of materials including one or more polymers.

As used herein, the term "toughness" refers to the ability of a material to absorb energy and plastically deform without fracturing. One definition of material toughness is the amount of energy per unit volume that a material can absorb before rupturing. It is also defined as a material's resistance to fracture when stressed.

As used herein, the term "glass transition" refers to the reversible transition in amorphous materials (or in amorphous regions within semicrystalline materials) from a hard and relatively brittle state into a molten or rubber-like state. An amorphous solid that exhibits a glass transition is called a glass.

As used herein, the term "crystallinity" refers to the degree of structural order in a solid. In a crystal, the atoms or molecules are arranged in a regular, periodic manner. The degree of crystallinity has a big influence on hardness, density, transparency and diffusion.

As used herein, the term "strain hardening" (also known as "work hardening and "cold working" refers to the strengthening of a material by plastic deformation. This strengthening occurs because of dislocation movements and dislocation generation within the crystal structure of the material.

EXAMPLES

Certain embodiments of the invention will now be discussed with reference to a series of examples. A number of possible alternative features are introduced in these examples. It is to be understood that, according to the knowledge and judgment of persons skilled in the art, such alternative features may be substituted in various combinations to arrive at different embodiments of the present invention.

Example 1: Process of Extraction of Polyhydroxyalkanoate from Microbial Cell Culture Methylotrophic bacteria are capable of utilizing simple one carbon substrates, such as methanol, methane, or other single carbon compound as their sole carbon and energy source. Methanol is a relatively inexpensive substrate, and has the added advantages of high solubility in water and low toxicity. Therefore, bacteria that can utilize methanol are of interest for a variety of applications involving methanol as a biofeedstock, including the biological production of fine chemicals and industrially important proteins. In certain embodiments of the present invention, the polyhydroxyalkanoates used for production of biofunctionalized films and coatings are produced by methylotrophic bacteria, such as bacteria from the genus *Methylobacterium*. *Methylobacterium extorquens* strain AM1 is a non-engineered representative strain capable of overproduction of polyhydroxyalkanoates in its native form. Other strains, genetically engineered or not, which are deemed to be effective at overproduction of polyhydroxyalkanoates may be used in alternative embodiments.

In one example embodiment of the inventive process, illustrated in FIG. 1, the polyhydroxyalkanoates used in production of bioactive films are produced by high density fermentation of a polyhydroxyalkanoate-producing microbial culture 10. The skilled person will understand that the treatment steps described below will include water washing steps at between the steps described below, to remove reagents from the cells and the desired polyhydroxyalkanoate material. The skilled person can determine the extent of water washing needed without undue experimentation and thus, specific water washing steps are not described in detail.

The culture 10 is centrifuged to separate the cells from the culture medium, followed by preparation of a suspension of the cells in water 12. In this particular embodiment, the suspended and washed cell mixture has an optical density between about 90 to about 110. The cells are then homogenized by using a mechanical homogenizer to produce a cell homogenate 14. Cellular debris 16 is discarded. In this particular embodiment, the homogenization is conducted at a pressure of 800 bar, and the cell suspension is transferred through the homogenizer. In certain embodiments, this process is repeated at least four times. Conventional cell disruption processes such as mixing with supercritical fluids technology, sonication or enzyme lysis techniques can be used to homogenize the cells.

The process continues with centrifugation of the homogenate to produce a crude polyhydroxyalkanoate pellet 18 and washing the pellet in water and then a solvent to produce a water and solvent washed mass of polyhydroxyalkanoate 20. This step removes lipids 22 from the crude material. In certain embodiments of the process, marketable lipid products 24 are purified from the lipids 22. In certain embodiments, the solvent system is composed of methanol, acetone and water (4:2:1). Organic solvents, such as chloroform, dichloroethane or methylene chloride, or cyclic carbonates, such as ethylene and propylene carbonates, can also be used to wash the polyhydroxyalkanoate. The solvent-washed polyhydroxyalkanoate 20 is then centrifuged to separate it from the solvent and solvent-washed polyhydroxyalkanoate 20 is then dispersed in water at a concentration of approximately 10% (w/w), followed by heating to about 80° C., under constant agitation.

The solvent washed polyhydroxyalkanoate product 20 is then bleached. In the present embodiment, hydrogen peroxide is used as the bleaching agent and is added to the heated solvent-washed polyhydroxyalkanoate 20 at a concentration of 3% (w/w) of the dispersion. The temperature of the dispersion is maintained at 80° C. for 3 hours to achieve complete bleaching of the polyhydroxyalkanoate and the bleached polyhydroxyalkanoate 26 is then heated to about 100° C. under constant agitation. The next step of the process is acid treatment. Hydrochloric acid is added to the dispersion of bleached polyhydroxyalkanoate 26 to achieve a concentration of 0.1 N HCl. The temperature of the dispersion is maintained at 100° C. for at least 1 hour. This is followed by cooling the dispersion to room temperature, subsequent centrifugation and water washing to remove residual acid. The result of this step is acid-treated polyhydroxyalkanoate 28.

The acid-treated polyhydroxyalkanoate is then dispersed, preferably at 10% (w/w) in a surfactant solution. In this particular embodiment, the surfactant solution is a 2.5% (w/w) sodium dodecyl sulfate solution which is heated to 40° C. under agitation. The temperature is maintained at 40° C. for at least 1 hour. The resulting surfactant-treated polyhydroxyalkanoate 30 is washed and dried. In this particular embodiment, a spray dryer with an inlet temperature of 175-185° C. and an outlet temperature of 95-110° C. is used to prepare dry polyhydroxyalkanoate powder 32 which is suitable as starting material for production of the biodegradable bioactive film or the biodegradable filament of the present invention.

Example 2: Formulation of Polymer Blends for Bioactive Films

This example describes the polymer blends and components thereof used in the manufacture of the bioactive films of the present invention. The classes of components of the polymer blends described hereinbelow provide the bioactive films with characteristics that support various embodiments of the bioactive film which may be used in various applications. The skilled person will understand that certain components may fulfill more than one of the functions described hereinbelow. The skilled person has the knowledge to identify certain components that have properties of more than one of the general categories outlined hereinbelow. For example, the skilled person will recognize that nanocrystalline cellulose may function both as a natural strengthening fiber and a nucleating agent.

Polyhydroxyalkanoates—

The main component of the bioactive film compositions of the present invention is provided by one or more polyhydroxyalkanoates. In certain embodiments, the polyhydroxyalkanoate is poly(3-hydroxybutyrate) or the copolymer poly(3-hydroxybutyrate)-co-valerate or a combination thereof. In certain embodiments, these polyhydroxyalkanoates are produced by bacteria and purified according to the process described in Example 1 and generally illustrated in FIG. 1. Different species and strains of bacteria may produce different polyhydroxyalkanoate polymers and these are also within the scope of the invention.

Bioactive Compounds and Microorganisms—

Bioactive compounds and/or microorganisms are included as components in embodiments of the bioactive film compositions. A bioactive compound or microorganism is any compound or microorganism that provides enhancement of any desirable biological function provided by the bioactive film. For example, the bioactive compound or microorganism may promote a particular aspect of the plant growth cycle or the bioactive compound or microorganism may promote growth of a desirable product or inhibit growth of one or more microorganisms that have negative effects on the desired biological function.

The type of bioactive compound or microorganism employed will depend upon the specific application of the bioactive film. Examples of bioactive compounds include fertilizers, nutrients, plant growth hormones and growth factors (such as auxins, gibberellins, cytokinins, abscisic acid, brassinosteroids, and ethylene, for example), metabolites, live microorganisms (such as, for example, members of the *Pediococcus, Bifidobacteria*, and *Lactobacillus* genera, which provide probiotic benefits and anaerobically ferment complex sugars of silage into lactic acid or probiotic microorganisms), inoculants, enzymes such as cellulases, hemicellulases and amylases, for example, which break down fibers and starches into simple sugars, and preservatives which inhibit growth of molds and yeast to prevent spoilage.

Nucleic acid-based inhibitors or modulators of gene expression are additional examples of bioactive compounds that can be employed with the films and coatings of the present invention. Such nucleic acid-based regulators or inhibitors of gene expression include small interfering RNAs (siRNAs), antisense compounds and microRNA compounds. These bioactive compounds can be used to inhibit or modulate gene expression to enhance growth of beneficial microorganisms such as soil amending bacteria or to inhibit growth of harmful microorganisms such as insects or pests. The skilled person can design appropriate nucleic acid-based inhibitors or modulators of gene expression as bioactive compounds for inclusion in the films and coatings of the present invention, without undue experimentation.

Plasticizers—

Incorporating plasticizers into the polyhydroxyalkanoate polymer blend is beneficial, as they function to decrease the melting temperature of the polymer blend. Examples of plasticizers which may be used for this purpose include glycerol, tributyl-O-acetylcitrate, glyceryl triacetate, bis(2-ethylhexyl) adipate, acetyl-tri-n-butyl citrate polyethylene glycol, sorbitol, mannitol and sodium monoleate. Decreasing the melting temperature allows for processing of the blend at lower temperatures, which leads to significant savings of energy resources and inhibits degradation of the material, and prevents deterioration of properties such as the molecular weight of the material. A further benefit of incorporating plasticizers is that the polymer blends have balanced crystallinity which increases ductility, and sharp melting behavior enhances material flow. Depending on the application of the bioactive film material, formulations may be produced with a plasticizer content of about 10-20% (w/w) to produce a film material with a high Young's modulus and high tensile strength. For other applications, the plasticizer content can also be increased up to about 30-40% (w/w), to produce a more ductile and more flexible film material.

Impact Modifiers—

One or more impact modifiers may also be blended with polyhydroxyalkanoates to modulate the properties of the film by increasing its impact strength. In some embodiments, these impact modifiers are derived from biological sources and are biodegradable. Examples of impact modifiers that may be used in embodiments of the bioactive film include starch, chitin, poly(butylene adipate co-terephthalate), polybutylene succinate, bio-based polyethylene, natural rubber and polylactic acid. Synthetically-derived polymers may also be used, examples of which are polycaprolactone, polyethylene, polypropylene, polyvinyl alcohol and polyvinyl acetate. A blend containing 20-30 wt. % impact modifiers can produce a material with high ductility and flexibility.

Natural Fibers—

Further improvement to the film properties may be achieved by incorporating natural fibers into the polymer blends as reinforcing agents. Examples of such natural fibers include, but are not limited to: nanocrystalline cellulose, microcrystalline cellulose, lignin, flax, hemp, bamboo and rice husk. Incorporation of any of these materials will improve the Young's modulus and tensile strength of the material while also accelerating biodegradation. Natural fibers may also be functionalized in order to increase their interaction with the polymer. Compatibilizers may also be added in order to improve the polymer-fiber adhesion. Crystalline nanocellulose fibers may also be modified through reactions including sulfonation, oxidation, cationization, or through grafting via acid chloride, acid anhydride and silylation. A composition of 10 wt % impact modifier and 10 wt. % natural fibers can be used to produce a polymer blend with balanced properties of flexibility and strength. Impact modifiers reduce the brittleness but lower the modulus of the polyhydroxyalkanoates, while natural fibers or other reinforcing agents increase the modulus of the composition.

Nucleating Agents—

Nucleating agents may be added to the polymer blend to enhance the crystallization of the polyhydroxyalkanoate base material. The addition of nucleating agents increases the crystallization rate, which allows optimal properties of the blend to be achieved in minimal time. Nucleating agents such as talc, mica, boron nitride, natural fibers including nanocrystalline cellulose and microcrystalline cellulose, sodium benzoate, calcium carbonate, silica, ionomers, clays, diacetal, titanium dioxide, various sorbitol derivatives such as dibenzylidene sorbitol, benzophenone, diacetal benzoate, lithium benzoate, sodium benzoate, potassium benzoate, thymine and the sodium salt of organophosphates may be used for this function.

Coagents—

Coagents may also be added to improve the crystallization kinetics of polyhydroxyalkanoates. In one embodiment, the reactive extrusion technique may be used to modify the properties of polyhydroxyalkanoates. Initiators such as peroxides may be used and the processing temperature controlled so as to induce decomposition of peroxides to produce free radicals, and unstable free radicals will remove hydrogen from the polyhydroxyalkanoate to produce additional free radicals. Coagents that have multiple functional groups will react with free radicals to form a branched structure, thus forming highly cross-linked, coagent-rich micron sized particles. Examples of coagents that may be used for this purpose are acrylic, styrenic, malemido, vinylic or allylic compounds such as triallyl trimestate, N,N-m-phenylenedimalemide, timethylpropane triacrylate, 1,2-polybutadiene, neopentylglycol diacrylate, diallylisophthlate, N-phenylmalemide and triallyl phosphate. These coagent particles will act as nucleating agents to enhance the crystallization rate of the polyhydroxyalkanoates and eliminate the requirement for incorporating a nucleating agent into the polymer blend, preventing the deterioration of polymer properties such as ductility that are typically affected by addition of nucleating agents. Another advantage of coagent modification using the reactive extrusion technique is that it will substantially improve the melt strength of the polyhydroxyalkanoates. The improved properties will allow polyhydroxyalkanoates to be processed through techniques such as thermoforming, film blowing and blow molding that involve stretching and melting of the polyhydroxyalkanoates or the polymer blend.

Antioxidants—

Antioxidants are used in formulations of certain embodiments of the invention to prevent thermal degradation of the polyhydroxyalkanoate during processing and to prevent oxidation of the film. One preferred antioxidant is pentaerythritol tetrakis(3-(3,5-di-tert-butyl-4-hydroxyphenyl) propionate). Other examples include, but are not limited to hindered amines, hindered phenol, phosphites and sulfur based antioxidants.

Fillers—

Fillers are particulate materials added to polymers in order to improve the physical properties and/or to reduce the cost of the composite. They can be classified according to their source, function, composition, and/or morphology. No single classification scheme is entirely adequate because of the overlap and ambiguity of these categories. The chemical composition and its effect on composite physical properties typically provide a basis for classifying fillers into three broad categories: nonreinforcing or degrading, semi-reinforcing or extending, and reinforcing fillers. The use of fillers in many commercial polymers is for the enhancement in stiffness, strength, dimensional stability, toughness, heat distortion temperature, color, damping, impermeability, and cost reduction, although not all of these desirable features are found in any single filled polymer. Improvements in composite physical properties are directly related to particle size, whereby the smaller particulate fillers impart greater reinforcement. Particle-size distribution and particle shape also have significant effects on composite reinforcement. Filler structure ranges from precise geometrical forms, such as spheres, hexagonal plates, or short fibers, to irregular masses. A particle with a high aspect ratio has higher reinforcement than a more spherical one. Fillers having a broad particle-size distribution have better packing in the polymer matrix and provide lower viscosity than that provided by an equal volume of the filler with a narrow particle-size distribution. The properties of particulate-filled polymers are determined by the properties of the components, by the shape of the filler phase, by the morphology of the system, and by the polymer-filler interfacial interactions. In certain embodiments, the fillers are biodegradable biological materials.

Reinforcing fillers and other special purpose filler additives, such as carbon nanotubes, microalgae biomass, cellulose fibrils, biochar and clays, may be added to the polymer blend for reinforcement. Transition metal oxobiodegradable additives may also be incorporated into the polymer blend. In response to sustained exposure to UV light and heat, these additives will induce fragmentation of the material, which will enhance the biodegradation rate. Adding biochar to the blend will allow for a black film material to be produced from a bio-sourced material, which is useful for producing a black mulch film or silage wrap that is compatible with organic agricultural practices. Adding clay will likewise allow an opaque film material to be produced, while blending dyes into the formulation will allow for films to be produced in a range of further colors. Conductive fillers such as steel fibers, carbon fibers, carbon nanotubes, graphite, graphene and carbon black may be incorporated into the polymer blend in order to impart electrical conductivity into the final formulations. Electrical conductivity provides a means to trigger release of a bioactive compound or microorganism held within the polymer. Other stimuli for triggering release of a bioactive compound or microorganism include, but are not limited to optical and chemical stimuli. In certain embodiments, if a stimulus is not provided, the bioactive compound or microorganism is released by passive diffusion during the biodegradation process.

Example 3: Formulation of Polymer Blends for Biodegradable Filaments

This example describes the polymer blends and components thereof used in the manufacture of the biodegradable filaments of the present invention. The classes of components of the polymer blends described hereinbelow provide the biodegradable filaments with characteristics that support various embodiments for use in various applications. The skilled person will understand that certain components of the polymer blends may fulfill more than one of the functions described hereinbelow. The skilled person has the knowledge to identify certain components that have properties of more than one of the general categories outlined hereinbelow. For example, the skilled person will recognize that, in certain embodiments, nanocrystalline cellulose may function both as a natural strengthening fiber and a nucleating agent. Certain embodiments include bio-based components to enhance the biodegradability of the polymer blend.

Advantageously, various embodiments of the biodegradable filament are characterized for mechanical properties including Young's modulus, tensile stress, tensile strain and impact strength, as well as thermal properties including glass transition temperature, melting temperature, crystallization temperature, total crystallinity, thermal stability, melt viscosity and strain hardening. Blend properties such as filler dispersion, blend morphology, and electrical conductivity are also characterized.

Exemplary embodiments of the biodegradable filaments of the invention are compostable in simple composting systems, have specific heat between about 1400-1600 J/Kg·K (vs 1800 J/Kg·K for PLA filaments) and thermal conductivity of 0.178 W/m·K (vs 0.13 W/m-K for PLA filaments) making them appropriate for three dimensional printing with lower energy requirements. These filament embodiments also have low glass transition temperatures of about 0-5° C., which allow them to be processed at lower temperatures. At room temperature, these blends are above the glass transition temperature and thus movement of the polymer chains is facilitated. The amorphous phase of the polymers in the filaments is rubbery at room temperature and this makes the filaments ductile.

Various compositions meet specific application requirements. Compositions containing lower amount of plasticizers (10-20 weight %) would have higher Young's modulus and tensile strength. Formulations containing up to 20% by weight of plasticizers remain in the form of free flowing powder and do not clog the extruder feeder. Compositions containing higher plasticizer content (30-40 weight %) are more ductile and will have higher elongation. Higher levels of plasticizers will reduce crystallinity of polyhydroxybutyrate yielding lower Young's modulus and tensile strength.

Formulations containing one or more coagents are expected to have improved crystallinity, melt viscosity and strain hardening properties. Coagents react with polymers and form long chain branches that provide improved melt strength. Coagents produce highly cross-linked particles which give a nucleating effect which results in improved crystallization kinetics.

Compositions with conducting fillers expected to have enhanced electrical properties. Conducting networks formed by fillers determines the conductivity level.

Polyhydroxyalkanoates—

The main component of the bioactive filament compositions of the present invention is provided by one or more polyhydroxyalkanoates. In certain embodiments, the polyhydroxyalkanoate is poly(3-hydroxybutyrate) or the copolymer poly(3-hydroxybutyrate)-co-valerate or medium chain-length polyhydroxyalkanoates or a combination thereof. In certain embodiments, these polyhydroxyalkanoates are produced by the methanotrophic bacterium *Methylobacterium extorquens* and purified according to the process described in Example 1 and generally illustrated in FIG. 1. Other bacteria, whether genetically engineered or not, may produce different polyhydroxyalkanoate polymers including short chain length, medium chain length and hybrid chain lengths. These polyhydroxyalkanoate polymers are also within the scope of the invention.

Plasticizers—

Incorporating plasticizers into the polyhydroxyalkanoate polymer blend is beneficial, as they function to decrease the melting temperature of the polymer blend. This will allow 3D printing to be achieved at lower temperatures, saving significant energy resources and inhibiting degradation of the material and the deterioration of properties such as the molecular weight of the material. Examples of plasticizers which may be used for this purpose include glycerol, tributyl-O-acetylcitrate, glyceryl triacetate, bis(2-ethylhexyl) adipate, acetyl-tri-n-butyl citrate polyethylene glycol, sorbitol, mannitol and sodium monoleate. A further benefit of incorporating plasticizers is that the polymer blends have lower crystallinity and glass transition temperature, which increases ductility. Addition of a plasticizer enhances the material flow. A high flow material yields faster printing and facilitates cleaning of the printer nozzle. Filament formulations may be produced with a plasticizer content of about 0.5-30% (w/w) to produce a filament material with a high Young's modulus and high tensile strength. For other applications, the plasticizer content can also be increased up to about 30-40% (w/w), to produce a more ductile and more flexible filament material.

Adhesives—

In certain embodiments, adhesives are incorporated into the filament formulations in order to improve adhesion properties and allow the use of the filament in dual nozzle printers configured for production of multicolored items. Attachment of first layer of polymer to a three dimensional printer platform is very crucial in order for an object to be successfully produced by a 3D printer. Typically, masking tape is used on 3D printer beds to achieve polymer attachment; however, the incorporation of an adhesive such as epoxy-based adhesives or functionalized polymers to improve the adhesive properties of the filament formulation provides a means for bonding of the polymer to the printer platform. Formulations containing an adhesive will also improve layer bonding of 3D printed components. This provides the advantage of eliminating the use of masking tape and other adhesives. Other examples of adhesives appropriate for inclusion in certain embodiments of the invention include, but are not limited to, polyurethanes, silicones, acrylates, polyvinyl acetate, and polyimides.

Strengthening Polymers—

One or more strengthening polymers (which are also known as "toughening agents" or "impact modifiers") may also be blended with polyhydroxyalkanoates to modulate the properties of the filament by increasing its impact strength. In some embodiments, these strengthening polymers are derived from biological sources and are biodegradable. Examples of strengthening polymers that may be used in embodiments of the filament include starch, chitin, poly (butylene adipate co-terephthalate), polybutyrate adipate terephthalate, polybutylene succinate, bio-based polyethylene, natural rubber, medium chain-length polyhydroxyalkanoates and polylactic acid. Synthetically-derived polymers may also be used, examples of which are polycaprolactone, polyamides, polyimides, polyethylene, polypropylene, polycarbonate, polyolefin, polyesters, polyvinyl alcohol and polyvinyl acetate and elastomers such as ethylene styrene, butylene styrene, and polyethylene octene. A blend containing 20-30% strengthening polymers as impact modifiers can produce a material with high impact strength.

Blends containing 20-30% by weight of impact modifiers will provide the filament with higher impact strength. Impact modifiers are dispersed in the polyhydroxybutyrate matrix and will absorb energy to prevent brittle failure. Compositions containing natural fibres will provide improved Young's modulus and tensile strength. Natural fibres will acts as reinforcing agents in polyhydroxybutyrate and they can also act as nucleating agents. Filament compositions containing about 20% by weight of an impact modifier and about 20% by weight of natural fibres provide balanced properties with sufficient elongation and strength and Young's modulus. Impact modifiers will improve the toughness at the cost of Young's modulus but addition of natural fibers can reverse this effect.

Toughening agents or "impact modifiers" are included in the formulations of the invention to compensate for the brittleness of polyhydroxyalkanoates and to improve ductility, toughness and tensile strain of the formulations. In the embodiments described herein, the toughening agents provide elasticity. Polybutyrate adipate terephthalate is a biodegradable elastomeric material with elongation greater than 500%. Polybutylene succinate is another promising candidate which is elastic and biodegradable. Examples of other toughening agents are starch, bio based polyethylene, natural rubber, polylactic acid and synthetic polymer such as polyamides, polyimides, polycarbonate, polyolefin, polyesters and elastomers such as styrene ethylene butylene styrene, polyethylene-octene elastomer. Polybutyrate adipate terephthalate mixes well with polyhydroxybutyrate and has demonstrated good compatibility with polyhydroxybutyrate.

Natural Fibers—

Further improvement to the filament properties may be achieved by incorporating natural fibers into the polymer blend as reinforcing agents. Examples of such natural fibers include, but are not limited to: nanocrystalline cellulose, microcrystalline cellulose, cellulose fibers, cellulose filaments lignin, flax, hemp, bamboo and rice husk. Incorporation of any of these materials will improve the Young's modulus and tensile strength of the material while also accelerating biodegradation. Natural fibers may also be functionalized in order to increase their interaction with the polymer. Composite filaments that include natural fibers offer improved strength, dimensional stability and provide fine surface texture which hides printing layers. This gives a superior aesthetic appearance to printed objects and allow for the introduction of different shades of color to the object by using different temperature profiles. Natural fibers may also be functionalized in order to increase their interaction with the polymer. Compatibilizers may also be added in order to improve polymer-fiber adhesion. Nanocrystalline cellulose can be modified through reactions including sulfonation, oxidation, cationization or grafting via acid chloride, acid anhydride and silylation. Compatibilizers may also be added in order to improve the polymer-fiber adhesion. Crystalline nanocellulose fibers may also be modified through reactions including sulfonation, oxidation, cationization, or through grafting via acid chloride, acid anhydride and silylation. A composition of 10% strengthening polymer as an impact modifier and 10% natural fibers can be used to produce a polymer blend with balanced properties of flexibility and strength. Impact modifiers reduce the brittleness but lower the modulus of the polyhydroxyalkanoates, while natural fibers or other reinforcing agents increase the modulus of the composition.

Nucleating Agents—

Nucleating agents may be added to the polymer blend to enhance the crystallization of the polyhydroxyalkanoate base material. The addition of nucleating agents increases the crystallization rate, which allows optimal properties of the blend to be achieved in minimal time. Nucleating agents such as talc, mica, boron nitride, natural fibers including nanocrystalline cellulose and microcrystalline cellulose, sodium benzoate, calcium carbonate, silica, ionomers, clays, diacetal, titanium dioxide, various sorbitol derivatives such as dibenzylidene sorbitol, benzophenone, diacetal benzoate, lithium benzoate, sodium benzoate, potassium benzoate, thymine and the sodium salt of organophosphates may be used for this function.

Coagents—

In certain embodiments, coagents are added to the filament compositions to improve the crystallization kinetics of polyhydroxyalkanoates. In one embodiment, the reactive extrusion technique may be used to modify the properties of polyhydroxyalkanoates. Initiators such as peroxides may be used at controlled processing temperature so as to induce decomposition of peroxides to produce free radicals. Unstable free radicals will remove hydrogen from the polyhydroxyalkanoate to produce additional free radicals. Coagents that have multiple functional groups will react with free radicals to form a branched structure, thus forming cross-linked, coagent-rich micron sized particles. Examples of coagents that may be used for this purpose are acrylic, styrenic, malemido, vinylic or allylic compounds such as triallyl trimestate, N,N-m-phenylenedimalemide, timethylpropane triacrylate, 1,2-polybutadiene, neopentylglycol diacrylate, diallylisophthlate, N-phenylmalemide and triallyl phosphate. These coagent particles will act as nucleating agents to enhance the crystallization rate of the polyhydroxyalkanoates and eliminate the requirement for incorporating a nucleating agent into the polymer blend, preventing the deterioration of polymer properties such as ductility that are typically caused by adding nucleating agents. Another advantage of using the reactive extrusion technique is that it will substantially improve the melt strength of the polyhydroxyalkanoates enabling their use in applications involving stretching of polymer melt such as thermoforming, film blowing and blow molding.

In order to modulate the molecular weight, crystallization properties and strain hardening, chain extenders may also be incorporated. The use of a reactive extrusion approach is preferable as it eliminates the requirement for nucleating agents. Coagent modification improves the crystallization rate and also prevents the deterioration of the polymer properties such as ductility that is caused by the addition of nucleating agents.

Fillers—

Fillers are particulate materials added to polymers in order to improve the physical properties and/or to reduce the cost of the composite. They can be classified according to their source, function, composition, and/or morphology. No single classification scheme is entirely adequate because of the overlap and ambiguity of these categories. The chemical composition and its effect on composite physical properties typically provide a basis for classifying fillers into three broad categories: nonreinforcing or degrading, semi-reinforcing or extending, and reinforcing fillers. The use of fillers in many commercial polymers is for the enhancement in stiffness, strength, dimensional stability, toughness, heat distortion temperature, color, damping, impermeability, and cost reduction, although not all of these desirable features are found in any single filled polymer. Improvements in composite physical properties are directly related to particle size, whereby the smaller particulate fillers impart greater reinforcement. Particle-size distribution and particle shape also have significant effects on composite reinforcement. Filler structure ranges from precise geometrical forms, such as spheres, hexagonal plates, or short fibers, to irregular masses. A particle with a high aspect ratio has higher reinforcement than a more spherical one. Fillers having a broad particle-size distribution have better packing in the polymer matrix and provide lower viscosity than that provided by an equal volume of the filler with a narrow particle-size distribution. The properties of particulate-filled polymers are determined by the properties of the components, by the shape of the filler phase, by the morphology of the system, and by the polymer-filler interfacial interactions. In certain embodiments, the fillers are biodegradable biological materials.

Coating Polymers—

Figure 4:
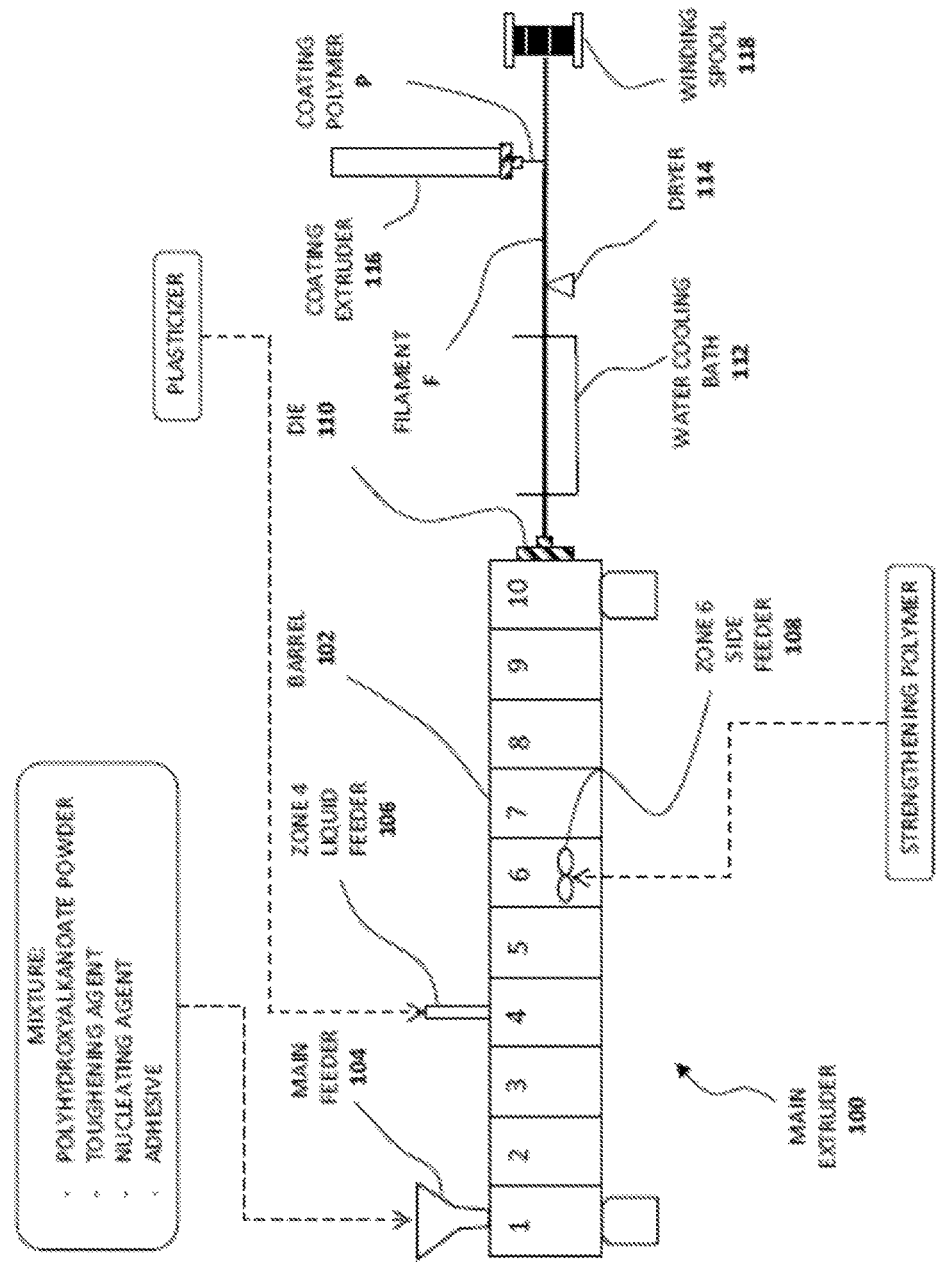
FIG. 4 is a process diagram for manufacture of a biodegradable filament using an extrusion process.

In some embodiments, the filament is coated with a coating polymer in order to provide a superior surface finish. Advantageously, the coating polymer had a low coefficient of friction, which improves flow and reduces the amount of force required to extrude the polymer. This facilitates unwinding of the filament from its spool and improves the look and feel of 3D-printed items. Additional polymer coatings can be applied on filament for various purposes. Polymer coatings can provide customized surface finishes to meet user requirements. It can provide a glossy surface or matte surface finish. Examples of polymer coatings include, but are not limited to paraffin wax, polyvinyl alcohol, ethylene vinyl acetate, polyvinyl acetate, ethylene acrylic acid, ethylene ethyl acrylate, ethylene methacrylate and ethylene methacrylic acid. In certain embodiments, an adhesive is provided between the blended formulation and the coating polymer to improve adhesion between the blended formulation and the coating polymer. In certain embodiments coating can be applied by the melt extrusion process as shown in FIG. 4. In certain embodiments low molecular weight polymer or plasticizers can be compounded in a filament formulation, these materials are non-compatible with polyhydroxyalkanoates and can migrate to the surface of the filament. This can provide a lubrication effect and reduce friction while the filament reaches the print head and also during unwinding from the 3D printing spool. This is particularly important in industrial 3D printers where the filament travels over a long distance. Specific low molecular weight polymers or plasticizers that migrate to the surface provide improved layer bonding.

In certain embodiments, the filament is a conductive filament and the coating is an electrostatic coating, such as the electrostatic coatings used in automotive painting. Electrostatic coatings provide friction reduction, non-stick surfaces, squeak reduction, release, corrosion, abrasion and wear resistance, conductivity, and shielding.

In certain embodiments 3D printing of conductive filaments is performed and the printed components are painted using an electrostatic painting technique.

Coloring Agents—

In certain embodiments, the filament is provided with one or more coloring agents or combinations thereof to provide diverse colors and improve its decorative appearance. Coloring agents are provided by dyes, pigments or any substance that will impart a color. Examples include, but are not limited to: organic pigments, organo-metallic pigments, mineral-based pigments, carbon pigments, titanium pigments, azo compounds, quinacridone compounds, phthalocyanine compounds, cadmium pigments, chromium pigments, cobalt pigments, copper pigments, iron pigments, clay earth pigments, titanium pigments, aluminum pigments, manganese pigments, ultramarine pigments, zinc pigments, tin pigments, iron oxide pigments, antimony pigments, barium pigments, biological pigments, dyes, photochromic pigments, conductive and liquid crystal polymer pigments, piezochromic pigments, goniochromatic pigments, silver pigments, diketopyrrolo-pyrrole compounds, benzimidazolone compounds, isoindoline compounds, isoindolinone compounds, and radio-opacifiers.

Examples of organic pigments include, but are not limited to: alizarin, anthoxanthin, arylide yellow, bilin, bistre, bone char, caput mortuum, carmine, crimson, diarylide pigment, Dragon's blood, Gamboge, Indian yellow, indigo dye, naphthol red, ommochrome, perinone, phthalocyanine Blue BN, phthalocyanine Green G, Pigment Yellow 10, Pigment yellow 139, Pigment Yellow 16, Pigment yellow 185, Pigment Yellow 81, Pigment yellow 83, quinacridone, Rose madder, Rylene dye, sepia ink and Tyrian purple.

Antioxidants—

Antioxidants are used in formulations of certain embodiments of the invention to prevent thermal degradation of the polyhydroxyalkanoate during processing and to prevent oxidation during the lifetime of the filament as well as three-dimensional printed objects formed from the filament. One preferred antioxidant is pentaerythritol tetrakis(3-(3,5-di-tert-butyl-4-hydroxyphenyl)propionate). Other examples include, but are not limited to hindered amines, hindered phenol, phosphites and sulphur based antioxidants.

Example 4: Extrusion Process for Forming a Bioactive Film

In this example embodiment, the bioactive film is manufactured using a twin-screw extruder constructed of customizable parts to provide a structure for optimal blending of formulation components prior to extrusion at the die of the extruder. The segmental design provides the ability to change the screw and barrel design in segments known as "zones." The screws are formed from a number of screw elements. The length of screw is selected according to the blending requirements of a particular application.

Figure 2:
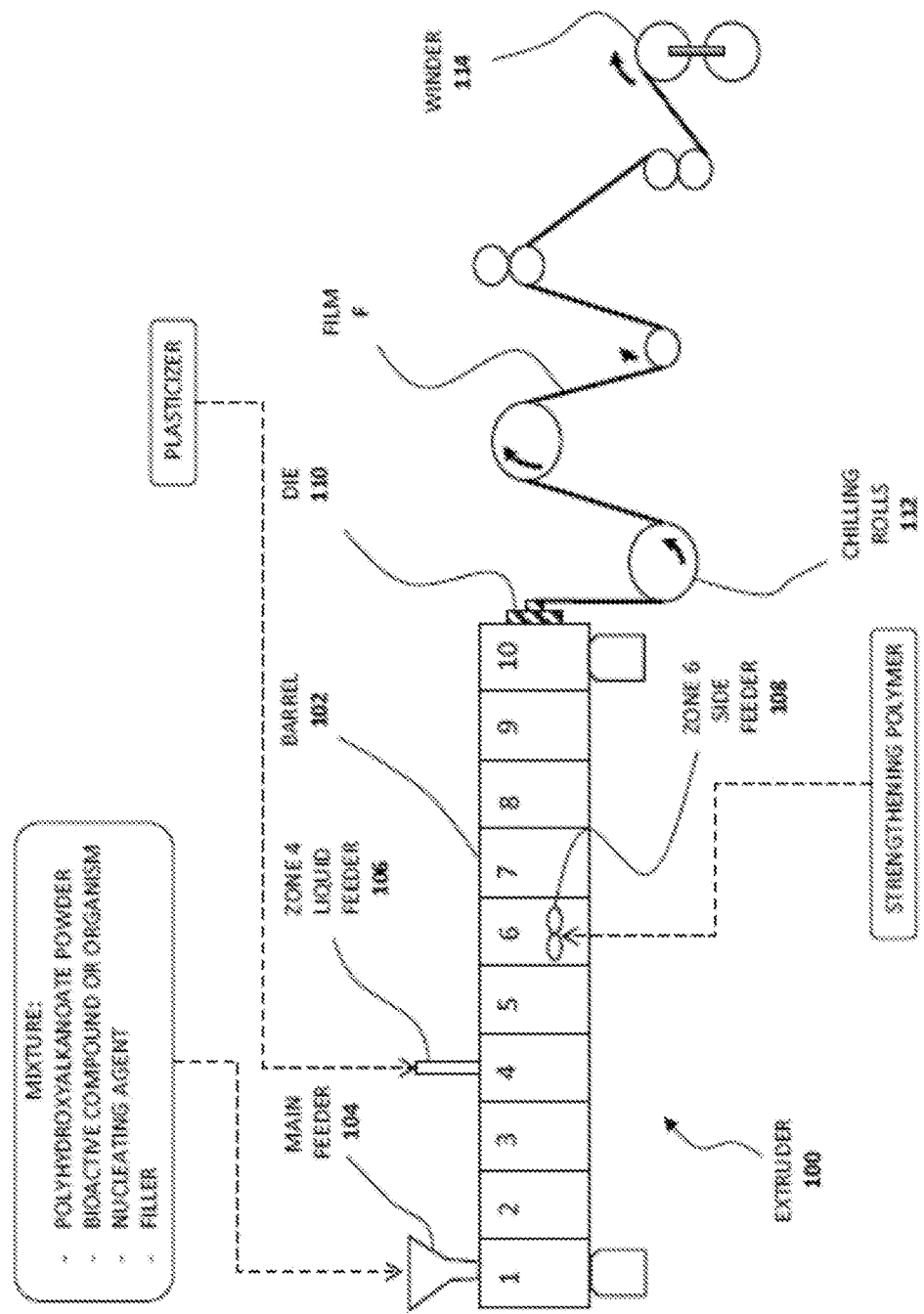
FIG. 2 is a process diagram for manufacture of a bioactive and biodegradable film using an extrusion process.

In one particular example embodiment shown in FIG. 2, the extruder 100 has a screw 100 cm long (not shown) which is formed of segments of 10 cm. Likewise, the barrel 102 has 10 segments, each 10 cm each in length, which form a barrel with a total of 10 zones (numbered 1-10 in FIG. 2). Zone 1 has the main feeder 104 attached thereto, for feeding of a mixture including the polyhydroxybutyrate, the bioactive compound or microorganism, the nucleating agent and the filler. Zone 4 is provided with a liquid feeder 106 for feeding of the plasticizer. Zone 6 is provided with a side feeder 108 for feeding of the impact modifier or fiber, which, in some embodiments is a natural fiber such as such as microcrystalline cellulose or nanocrystalline cellulose, lignin, flax, hemp, bamboo or rice husk. The downstream feeding of the natural fiber minimizes fiber attrition and maintains the aspect ratio of the fibers. Therefore, the pre-mixed feed is first mixed with the plasticizer in Zone 4 and then the impact modifier or fiber in Zone 6. In certain alternative embodiments, the impact modifier or fiber is fed at one of the further downstream zones. The mixture emerges from the die 110 as a film F which is cooled at chilling rolls 112 and then rolled over a downstream series of rollers before it enters a winder 114 for winding on a spool.

In the present example embodiment, the components of the main feed mixture are individually dried in a hot air oven, vacuum oven or dehumidifier at 100° C. for a minimum of 3 hours followed by weighing and dry mixing in a batch mixer or tumbler, prior to further compounding in the extruder 100.

Processing parameters including screw design and screw speed particularly influence the dispersion and distribution of natural fibers in polymer. In certain embodiments, the screw design has only two sets of kneading blocks to avoid breaking fibers and at least four mixing elements are incorporated to produce intense shear to achieve homogenous mixing.

In certain embodiments, reverse elements between the forward conveying elements are used to improve mixing without generating high shear. The specific screw design produces specific geometry of natural fibers in a polymer.

In one specific embodiment, the following conditions are employed: Screw diameter: 25 mm, L/D: 40, Temperatures: Zone 1—100° C.; Zone 2—160° C.; Zone 3—170° C.; Zone 4—175° C.; Zone 5—180° C.; Zone 6—180° C.; Zone 7—175° C.; Zone 8—170° C.; Zone 9—165° C.; Zone 10—160° C.; and Die—160° C. The screw speed is 100 rpm.

In certain embodiments, after extrusion, the molten plastic exiting the die is fed to chilling rolls and the die is reoriented to guide the flow of the melted polymer from the extruder to a thin, flat planar flow rolling system to form the film. The film is then wound onto spools.

Example 5: Extrusion Process for Forming a Biodegradable Filament

In this example, the extrusion process is generally similar to that of Example 4. However, the process is configured to have the extruded mixture emerging from the die 110 as a filament F which is cooled in a water cooling bath 112, and dried with an air blade or air gun dryer 114. In this particular embodiment, the filament F is provided with a coating polymer P emerging from a coating extruder 116 before it is wound on a spool 118. In alternative embodiments, the filament is cooled in air rather than in a water bath if it is deemed that water drying is not advantageous. In certain embodiments, the die used to form the filament F has an opening diameter of 1.75 mm or 3 mm. The spools may be of various sizes, for example spools configured to hold spooled filament masses of 0.25 kg, 0.5 kg, 0.75 kg, 1 kg, 2 kg, 5 kg, 10 kg, 25 kg, 50 kg to 100 kg.

This embodiment of the process is projected to produce a filament with sufficient rigidity to maintain consistent roundness to preserve proper functioning within the 3D printer. The filament is projected to retain a uniform diameter over its length, which ensures accurate 3D printing. In certain embodiments, the branching introduced by coagents in the formulation enhances the rigidity. Controlled crosslinking is also projected to provide additional strength to the filament.

In the present example embodiment, the blend components of the main feed mixture are individually dried in a hot air oven, vacuum oven or dehumidifier at 100° C. for a minimum of 3 hours or at 60° C. for overnight followed by weighing and dry mixing in a batch mixer or tumbler, prior to further compounding in the extruder 100.

Processing parameters including screw design and screw speed particularly influence the dispersion and distribution of natural fibers in polymer. In certain embodiments, the screw design has two sets of kneading blocks to avoid breaking fibers and at least four mixing elements are incorporated to produce intense shear to achieve homogenous mixing.

In certain embodiments, reverse elements between the forward conveying elements are used to improve mixing without generating high shear. The specific screw design produces specific geometry of natural fibers in a polymer.

In certain embodiments, after extrusion, the molten plastic exiting the die is passed through a water cooling bath. The filament is then wound onto a spool.

In alternative embodiments, a polymer coating is applied while the filament is hot.

Example 6: Casting of a Polyhydroxybutyrate Base Film

As a proof-of-concept experiment, a polyhydroxybutyrate film was produced using a solution casting technique. A 5 g mass of polyhydroxybutyrate with molecular weight of 300,000 Da and particle size of 200 μm was solubilized in 100 g of chloroform and the solution was poured into a petri dish. The solvent was evaporated and the resulting polyhydroxybutyrate film was dried at room temperature. The film was translucent, flexible, and resistant to breakage after bending and straightening at least 20 times. This initial experiment indicates that resilient films can be produced using polyhydroxybutyrate as the main polymer material.

Example 7: Bioactive Mulch Film

The present example describes one embodiment of a mulch film suitable for improving crop yield and quality. The polymer formulation of this mulch film is projected to provide sufficient flexibility and strength suited to facilitate installation of the film on crop rows together with biodegradability to allow the film to break down in the soil after it is removed from the crop rows.

The mulch film of this particular example embodiment includes polyhydroxyalkanoate as a major component, a plasticizer, a relatively inexpensive reinforcing filler which also acts as a coloring agent, the plant growth hormone auxin as a bioactive compound, a nucleating agent, and an impact modifier or fiber. The formulation provides the properties required for generation of a resilient mulch film. Charcoal serves a dual purpose, acting as a filler to lower the formulation cost and providing the black color desired for mulch films. Ranges of components for this mulch film embodiment are provided in Table 1 below.

TABLE 1

Bioactive Mulch Film Composition

| Component Category | Component | Range |
| --- | --- | --- |
| Polyhydroxyalkanoate | Poly(3-hydroxybutyrate) | 65%-75% |
| Plasticizer | Glycerol | 10%-20% |
| Nucleating Agent | Boron nitride | 0.2%-1% |
| Bioactive Compound | Auxin (plant growth hormone) | 0.01%-0.05% |
| Filler | Charcoal | 1%-5% |
| Impact modifier | Polybutyrate adipate terephthalate | 10%-20% |
| Antioxidant | Pentaerythritol tetrakis(3-(3,5-di-tert-butyl-4-hydroxyphenyl)propionate) | 0.1%-1% |

The properties projected for this composition are: tensile strain: 25-100%; tensile strength: 20-25 MPa; tensile modulus: 500-800 MPa; tear resistance (Elmdorf): 100-200 g; dart impact: 100-200 g; oxygen permeability <1 $cm^3/m^2$ day (23° C./85% r.h.) and water vapor permeation rate 1500 1500 $g/m^2 \cdot d$ (at 38° C., 905 r.h.).

This embodiment and other similar embodiments of mulch films are expected to be effective in suppressing weeds and controlling loss of nutrients and water loss from the soil while boosting the productivity of their crops by at least 15-25%. Polyhydroxyalkanoate-based films are expected to be effective as weed management tools, limiting weed growth by forming a physical barrier above the soil and by blocking sunlight from reaching growing weeds. Plastic mulch is also an important tool for limiting losses due to drought, helping crops to survive drought stress by limiting evaporative water loss from soils and by blocking the growth of weeds that otherwise would draw moisture away from the target crop. The significant expense and labor associated with the removal and disposal of their spent mulch films produced from non-biodegradable plastics is avoided by simply plowing the spent mulch film into the soil where it undergoes biodegradation. Alternative embodiments of the mulch film further include bioactive metabolites or live microorganisms which enhance the rate of biodegradation.

Example 8: Multi-Layer Bioactive Mulch Film

In this example, a bioactive mulch film is formed of three layers, each having a different bioactive compound. The bioactive compound may be blended into the film during processing, or alternatively it may be incorporated in between the film layers. In alternative embodiments, fewer or more than three layers are provided with similar or different bioactive compounds placed between or blended within the different layers. In this particular example, auxin (a plant growth hormone involved in seed germination) dispersed on an upper surface of a first layer before placement of a second layer. This provides auxin sandwiched between the first and second layers. Eventual degradation of this first plant-contacting layer over the course of a plant growth period releases auxin into the soil to enhance germination of the plant. Subsequently the second layer degrades as desired, optionally with an artificial or natural stimulus which then causes release of a cytokinin which acts as a stem elongation factor to enhance the stem-forming stage of plant growth. Such compositions may be customized for various crops and soil conditions.

In certain embodiments, cross-linking of polyhydroxyalkanoates or the incorporation of additives allows a film material to be produced that requires a shorter or longer period of time to decompose, which will allow the different layers to release their bioactives at different rates to correspond to plant growth requirements. Addition of stabilizing additives may also allow production of a mulch film product that can be used for multiple growing seasons.

In other embodiments, a leaf vein or mesh-structured channels may be incorporated into the film layer to allow for delivery of agents to trigger biodegradation.

In other embodiments, a leaf vein or mesh-structured natural fiber additive is used to enhance the controlled release of bioactive compounds or microorganisms during the polymer degradation process.

In other embodiments, pesticides that are capable of suppressing the growth of insects, fungi, weeds, or other pests are included as bioactive compounds. The pesticides may belong to any of the following classes: herbicides, algicides, avicides, bactericides, fungicides, insecticides, miticides, molluscicides, nematicides, rodenticides and virucides.

The provision of a multi-layer biodegradable film for carrying a series of bioactive compounds and/or microorganisms provides the ability to fine-tune the film for various conditions because each layer of the film can be engineered to biodegrade at a desired rate to match the particular growth dynamics of a given plant for which the multi-layer biodegradable film is manufactured.

Biodegradability may be controlled by additives that could be triggered by external or environmental stimuli. For example, layers with additional starch may degrade at a faster rate when there is an excess of water. Starch may also be provided between layers to add strength and/or bulk. Temperature sensitive triggers may be provided for release of cryopreservation factors. Polyhydroxyalkanoates are microbial energy and carbon storage molecules which requiring microbial activity for degradation. Therefore, strategic incorporation of anti-microbial agents within certain film layers, or on the surfaces of the film layer is a useful strategy for controlling the rate of degradation and release of bioactive compounds located between layers Certain layers of the multi-layer film include microorganisms which may be in the form of spores that influence the local microflora and to provide a desirable effect for promotion of plant growth or prevention of growth of weeds, for example.

Multi-layer film may include a hydrogel or other thermo-protectant for protecting bioactives as well as passive diffusion enhancers and active functionalized molecules that are released in response to an environmental stimulus. For example, the release of a bioactive or film degradation in a particular layer of film may be triggered by particular wavelengths of light from controlled light sources.

Example 9: Bioactive Multi-Purpose Film

Multipurpose film can be used to protect plants and trees from extreme weather conditions and can also be used as packaging material during transportation. The film will also be used a delivery vehicle for natural biostimulants and biocides that are projected to increase crop yields by about 30%. The film can be used to wrap a wounded region of tree and slowly release bioactive compounds or microorganisms such as plant growth hormones or probiotic microorganisms, for example.

The multipurpose film of this particular example embodiment includes polyhydroxyalkanoate as a major component, a plasticizer, a relatively inexpensive reinforcing filler which also acts as a coloring agent, a bioactive compound, a nucleating agent, and an impact modifier or fiber to provide properties suitable for generation of a film. Ranges of components for this mulch film embodiment are provided in Table 2 below.

TABLE 2

Bioactive Multi-Purpose Film Composition

| Component Category | Component | Range |
|---|---|---|
| Polyhydroxyalkanoate | Poly(3-hydroxybutyrate) | 65%-75% |
| Plasticizer | Glycerol | 10%-20% |
| Nucleating Agent | Boron nitride | 0.2%-1% |
| Bioactive micro-organisms | Probiotic micro-organisms | 0.01%-0.05% |
| Filler | Clay | 1%-5% |
| Impact modifier | Polybutyrate adipate terephthalate | 10%-20% |
| Antioxidant | Pentaerythritol tetrakis(3-(3,5-di-tert-butyl-4-hydroxyphenyl)propionate) | 0.1%-1% |

The properties projected for this composition are: tensile strain: 25-100%; tensile strength: 20-25 MPa; tensile modulus: 200-500 MPa; tear resistance (Elmdorf): 50-100 g; dart impact: 100-200 g; oxygen permeability <1 $cm^3/m^2$ day (23° C./85% r.h.); water vapor permeation rate 1500 $g/m^2 \cdot d$ (at 38° C., 905 r.h.); surface resistivity: 30,000-40,000 Ohms/square; and volume resistivity: 30,000-40,000 Ohms·cm.

In certain embodiments, the multipurpose film is used as a silage wrap which provides a biodelivery vehicle for bioactive metabolites, inoculants or live probiotic microorganisms which stimulate fermentation of forages to enhance the quality of the feed. In certain embodiments, the multipurpose film also includes antimicrobial compounds which specifically inhibit growth of microorganisms that cause detrimental effects to the wrapped feed.

Example 10: Bioactive Electrically-Conductive Film

Bioactive electrically-conductive film is designed to be wrapped around trees and other crops. Electricity and/or light can be passed through the electrically-conductive film to generate heat, which will trigger the release of the bioactive compounds or microorganisms. Under cold weather conditions, the heat produced will also keep the tree or crop warm. This is expected to improve the resiliency of trees and crops during cold weather conditions.

The bioactive electrically-conductive film of this particular example embodiment includes polyhydroxyalkanoate as a major component, a plasticizer, a relatively inexpensive reinforcing filler (which also provides electrical conductivity), a bioactive compound, a nucleating agent, and an impact modifier or fiber. This formulation is projected to provide characteristics suitable for generation of a bioactive electrically-conductive film. Ranges of components for this mulch film embodiment are provided in Table 3 below.

TABLE 3

Bioactive Electrically-Conductive Film Composition

| Component Category | Component | Range |
|---|---|---|
| Polyhydroxyalkanoate | Poly(3-hydroxybutyrate) | 65%-75% |
| Plasticizer | Glycerol | 10%-20% |
| Nucleating Agent | Boron nitride | 0.2%-1% |
| Bioactive Compound | Auxin (plant growth hormone) | 0.01%-0.05% |
| Filler | Carbon black (electrically-conductive) | 1%-5% |
| Impact modifier | Polybutyrate adipate terephthalate | 10%-20% |
| Antioxidant | Pentaerythritol tetrakis(3-(3,5-di-tert-butyl-4-hydroxyphenyl)propionate) | 0.1%-1% |

The properties projected for this composition are: tensile strain: 25-100%; tensile strength: 20-25 MPa; tensile modulus: 200-500 MPa; tear resistance (Elmdorf): 50-100 g; dart impact: 100-200 g; oxygen permeability <1 $cm^3/m^2$ day (23° C./85% r.h.), water vapor permeation rate 1500 $g/m^2 \cdot d$ (at 38° C., 905 r.h.); surface resistivity: 30,000-40,000 Ohms/square; volume resistivity: 30,000-40,000 Ohms·cm.

Example 11: Bioactive Film for Use in Plant Propagation and Plant Wound Treatments In this example, a bioactive film for use in plant propagation and plant wound treatments is described. The process of air layering is well known in the horticultural arts as a method of plant propagation. In this method, a target region of a plant or tree shoot is wounded and a strip of bark removed. A moisture-encasing medium, such as sphagnum moss, is typically wrapped around the wound. Plastic films are typically wrapped around the sphagnum moss to provide a moisture barrier while a rooting hormone, such as members of the auxin plant growth regulator family, is added to encourage the wounded region to grow roots. After roots form, the plastic is removed and the target region is excised from the parent plant and planted. In an embodiment of the present invention, the barrier plastic is the polyhydroxyalkanoate-based bioactive film designed to slowly release the bioactive compound from the film into the wounded region.

The bioactive film of this particular example embodiment includes polyhydroxyalkanoate as a major component, a plasticizer, an organic filler which provides a nutrient source for microorganisms that contribute to the biodegradation of the film, a bioactive compound, a nucleating agent, and an impact modifier. This formulation is projected to provide characteristics suitable for generation of a bioactive film for use in plant propagation methods. Ranges of components for this mulch film embodiment are provided in Table 4 below.

TABLE 4

Bioactive Film Composition for use in Plant Propagation

| Component Category | Component | Range |
| --- | --- | --- |
| Polyhydroxyalkanoate | Poly(3-hydroxybutyrate) | 65%-75% |
| Plasticizer | Glycerol | 10%-20% |
| Nucleating Agent | Boron nitride | 0.2%-1% |
| Bioactive Compound | Auxin (plant growth hormone) | 0.01%-0.05% |
| Filler | Algae | 1%-5% |
| Impact modifier | Polybutyrate adipate terephthalate | 10%-20% |
| Antioxidant | Pentaerythritol tetrakis(3-(3,5-di-tert-butyl-4-hydroxyphenyl)propionate) | 0.1%-1% |

In this embodiment, auxin is incorporated into the film and is slowly released into the plant tissue to enhance plant growth. This avoids the requirement for directly adding auxin to the wound region on the plant.

After roots have formed, the excised target region may be planted into the soil with the plastic barrier still present. As the polyhydroxyalkanoate-based wrap decomposes in the ground it will provide nutrients to the growing plant.

Example 12: Bioactive Coating or Film for Interior Lining of Tree Tubes

In this example, a bioactive coating or film is used as a tree tube liner which releases a pesticide. Tree tubes are employed to protect trees during early stages of growth, providing a physical barrier that resists herbivore attack and blocks weed growth. In this example embodiment, a tree tube is lined with a polyhydroxyalkanoate-based coating material that supplies the tree with pesticides that suppress the growth of pathogens or weeds, growth-promoting bioactive metabolites or with microorganisms that promote plant growth and suppress the growth of pathogens or weeds.

The bioactive film of this particular example embodiment includes polyhydroxyalkanoate as a major component, a plasticizer, an inexpensive filler, a pesticide as a bioactive compound, a nucleating agent, and an impact modifier. This formulation is projected to provide characteristics suitable for generation of a bioactive film for use in plant propagation methods. Ranges of components for this mulch film embodiment are provided in Table 5 below.

TABLE 5

Bioactive Coating or Film for Interior Lining of Tree Tubes

| Component Category | Component | Range |
| --- | --- | --- |
| Polyhydroxyalkanoate | Poly(3-hydroxybutyrate) | 65%-75% |
| Plasticizer | Glycerol | 10%-20% |
| Nucleating Agent | Boron nitride | 0.2%-1% |
| Bioactive Compound | d-limonene | 0.01%-0.05% |
| Filler | Clay | 1%-5% |
| Impact modifier | Polybutyrate adipate terephthalate | 10%-20% |
| Antioxidant | Pentaerythritol tetrakis(3-(3,5-di-tert-butyl-4-hydroxyphenyl)propionate) | 0.1%-1% |

In this embodiment, d-limonene is incorporated into the film as an insecticide and is slowly released from the film to protect the tree from attack by insects.

Example 13: Bioactive Biodegradable Seed Coatings

In this example, embodiments of bioactive seed coatings are described. Modern agriculture practices and the changing climate make it desirable that the seeds contain specific protections against premature germination to enhance uniformity in crop growth rates and to optimize production timetables. Encapsulation of seeds may be conducted to protect seeds and germinating seedlings against pest damage, to provide delivery of active ingredients such as insecticides, fertilizers, active ingredients, soil amending or other beneficial chemicals or microorganisms as well as to protect the seeds against abrasion during shipping, storage and broadcasting. Seed coatings also increase the size of small or irregularly shaped seeds, which makes broadcasting more efficient, as well as sealing cracks or defects in the hull or surface of seeds, which prevents the entry of moisture, mold or bacteria that can spoil the seed. Agricultural chemicals, such as fungicides, herbicides, insecticides and bird repellents blended into seed coatings improve the viability of the seed and to protect the growing plant. Controlled release of active compounds increases efficiency in use and reduces non-target impacts. The seed coating formulations of this example include a bioactive compound or microorganism which is released by the biodegradation, rupture or dissolution of the coating. Alternatively, the coating or membrane is porous and semipermeable to allow active ingredient to diffuse out and water and other minerals from the soil can diffuse inside the coating and make contact with the seed. Single or multiple layers of coatings are provided to control coating decay rates according to the requirements of various seeds.

The bioactive compounds and microorganisms, (which may be considered to function as biostimulants for enhancement of growth plants from the seeds) included in the coatings are any of those described hereinabove and more particularly, agricultural chemicals, insecticides, rodenticides, nematocides, miticides, bird repellents, fertilizers, soil amending microorganisms, or nucleic acid-based inhibitors or modulators of gene expression, such as antisense compounds, siRNAs or microRNA compounds. The microorganisms may be in the form of dormant or live spores of bacteria, non-sporulating bacteria, archae or fungi. The microorganisms may be attached to the polyhydroxyalkanoate polymer via a biomolecular attachment mechanism such as that provided by an antibody, for example. In some cases, additives such as osmoprotectants and carbohydrates are blended along with the microorganisms that protect them during the encapsulation process that would otherwise kill the microorganisms.

Solvent-Based Coating Method—

In one particular example of a process for coating seeds, dried polyhydroxyalkanoate obtained as described above is mixed with an organic solvent and one or more additives to solubilize the polyhydroxyalkanoate polymer in a mixture.

To reduce the exposure of the bioactive compound or microorganism to the solvent systems or high temperature in the case of melt coating, seeds may first be coated with the polymer solution/melt and its additives without incorporating the bioactive compound or microorganism. The bioactive compound or microorganism may then be applied to the coated seeds. Advantageously, this is performed prior to complete drying of the coating on the seeds surface to allow the bioactive compound or microorganism to become embedded in the polymer network. Such an approach will promote a quicker release of the active ingredients.

In some embodiments, natural macromolecules such as starch, pectins, proteins (such as gelatin, casein, collagen, soy protein, corn gluten, and algal proteins) are blended with the polyhydroxyalkanoates for the coating. The following steps are employed: (1) the natural macromolecules together with additives such as plasticizers are prepared in one container, (2) the polyhydroxyalkanoate solution is prepared in a separate container, (3) The two solutions are mixed and agitated together at high speed to disperse the molecules and form fine emulsions. The emulsion is then used as a seed coating formulation. The active ingredients are incorporated either in the blend preparation step or later after the coating was applied on the seed surface. The purpose of blending natural macromolecules with polyhydroxyalkanoates not only improves the economics of preparation of the coating material, but also enhances the biodegradation rate, improves water permeability of the coating, and boosts the release rate of active ingredients from the coating.

In certain embodiments, seeds are encapsulated by the coating based on a short or medium chain length of polyhydroxyalkanoate. Medium chain-length polyhydroxybutyrate has an average chain length of about 6 to about 14 carbon atoms. Short chain-length polyhydroxyalkanoate has an average chain length of about 3 to about 5 carbon atoms. The short or medium chain length polyhydroxyalkanoate has better solubility in a number of solvents relative to long chain length polyhydroxyalkanoate. Increasing the range of solvents increases the possible solvents bioactive compound or microorganism and additives. The choice of solvent depends upon the stability of the mixture formed. Example solvents include, but are not limited to chloroform, dichloromethane, 1,2,2-tetrachloroethane, ethylene carbonate, propylene carbonate, acetic anhydride, N,N-dimethylformamide, ethylacetoacetate, acetic acid, 2,2,2-trifluoroethanol, a higher alcohol having more than three carbon atoms, dioxane, toluene, pyridine, benzene, acetone, tetrahydrofuran, diethyl ether, n-hexane, 2-propanol and xylene. Also, the low melting temperature of medium chain-length polyhydroxyalkanoates (30-60° C.) may allow melt coating of the seeds and active ingredients with the risk of destroying the seeds and/or the functionality of the bioactive compound or microorganisms. In applications where both the seeds and the active ingredient are resistant to high temperature, melted short chain polyhydroxyalkanoates may be used as a coating material.

Figure 3:
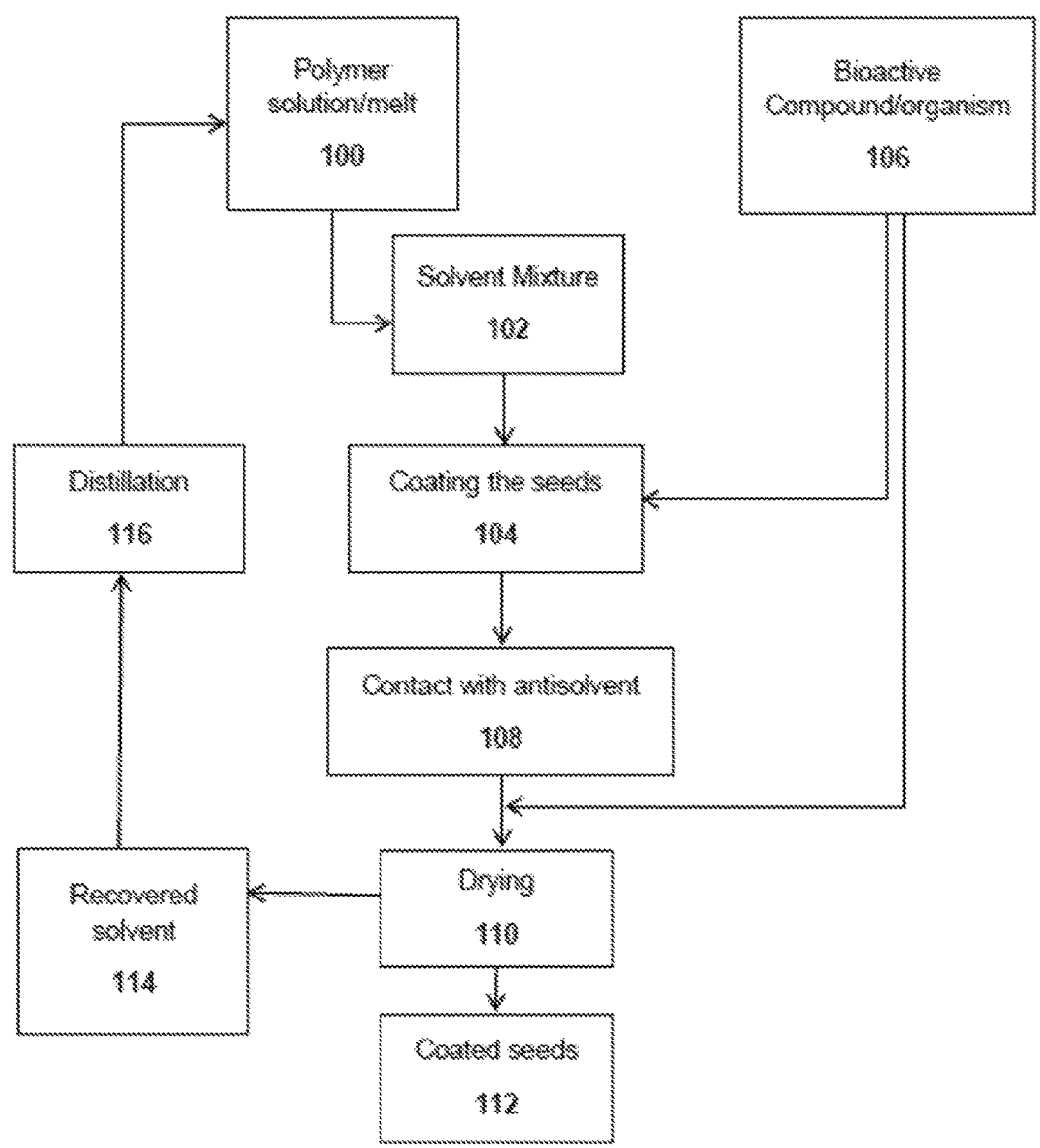
FIG. 3 is a process diagram for providing seeds with a biodegradable polymer coating.

In some embodiments, pore porosity of the coating is controlled by controlling solvent evaporation or by contacting the coating with a pore producing agent. The pore producing agent is provided by an anti-solvent for the polyhydroxyalkanoate in some cases, such as water for example. An example of a method using control of pore porosity is illustrated in FIG. 3. A polymer solution containing polyhydroxyalkanoate 100 is mixed with a solvent to produce a solvent mixture 102 which is used to coat seeds 104, for example, by soaking the seeds for about 1-20 minutes. The bioactive compound or microorganism 106 is then applied to the coated seeds 104. An antisolvent, such as water, methanol or ethanol is applied to the coated seeds 108 in a controlled manner to control the size of pores in the coating. The contact time between the pore producing agent and the coated seeds may vary between as little as 1 min to as long as 24 hrs. The treatment displaces the organic solvent from the coated polymer and may produce a coagulating effect allowing the pore producing agent to come in between the coating. The pore producing agent is then evaporated to leave behind a porous coating.

The seeds are subjected to a drying process 110 to obtain the final coated seed product 112. In an optional solvent recovery process, the recovered solvent 114 is distilled 116 and recycled for use in preparation of the polymer solution 100.

An alternative to the soaking process is spray coating. The polymer solution is atomized and sprayed onto the surface of the seeds.

It is advantageous in certain cases to include additives in the mixture such as starch, pectin, one or more proteins, a plasticizer and an antioxidant, such as those described hereinabove.

Hydrogel-Based Coating Method—

In this example, the polyhydroxyalkanoate is modified to form an amphiphilic (water-soluble) material that can be formed into a hydrogel. The polyhydroxyalkanoate is used to generate a triblock copolymer (including polyethylene glycol, polypropylene glycol or other similar polymers) which is then mixed with an α-cyclodextrin according to a known method (Li and Loh, 2015, Chemistry Society Reviews, 44:2865-2879, incorporated herein by reference in its entirety). This approach may be particularly useful for controlled delivery of nucleic acid-based bioactive compounds to seeds. A number of different approaches for modifying polyhydroxyalkanoates have been outlined, and these approaches may be useful for functionalizing hydrophobic polyhydroxyalkanoates into colloidal systems, such as hydrogels, that may be used to encase bioactive compounds or microorganisms around a seed. By altering the hydrophilicity of the colloid, the rate of biodegradability of the coating may also be controlled.

Microporous Sponge Coating—

In this example, the bioactive compound or microorganism is encased within microporous material, which would offer protection during the encapsulation process. A spray drying technology can be adapted to produce a porous form of polyhydroxyalkanoate that may be adapted for this purpose. The microporous polyhydroxyalkanoate layer is deposited on the seed by spray-drying and the then a solution containing the bioactive compound or microorganism is sprayed on the microporous layer, followed by washing. This causes the bioactive compound or microorganism to become wedged into the microporous structure. The porosity allows water to enter while protecting the seed. In alternative embodiments, a relatively non-porous coating layer is first deposited followed by the deposition of the microporous layer to provide an additional protective inner layer.

Example 14: Flexible Filament

The present example describes one embodiment of a flexible filament. This formulation provides sufficient ductility required for general purpose filaments that can be used to print any household or industrial functional component and provide printing material for the three-dimensional printing hobbyist community.

The target properties for one embodiment of a flexible filament are: tensile strain: 25-100%; tensile strength: 30-50 MPa; Young's modulus: 200-500 MPa; and Izod impact strength: 10-30 KJ/m$^2$ Ranges of components for this polymer filament embodiment are provided in Table 6 below.

TABLE 6

Flexible Filament Formulation

| Component Category | Component | Percent Range (% m/m) |
| --- | --- | --- |
| Polyhydroxyalkanoate | Poly(3-hydroxybutyrate) | About 50% to about 70% |
| Toughening Agent | Polybutyrate adipate terephthalate | About 30% to about 50% |
| Plasticizer | Acetyl tri-n-butyl citrate | About 10% to about 30% |
| Nucleating Agent | Boron nitride | About 0.1% to about 1% |
| Coloring Agent | Organic pigment | About 0.01% to about 1% |
| Antioxidant | Pentaerythritol tetrakis(3-(3,5-di-tert-butyl-4-hydroxyphenyl)propionate | About 0.1% to about 1% |
| Adhesive | Epoxy-based adhesive | About 0.01% to about 2% |

Example 15: High Strength Filament

The filament of this example has a composition providing high strength for three-dimensionally printed items such as tools and reinforcing members. Nanocrystalline cellulose used in composition provides outstanding strength in a low concentration range. Calcium carbonate reduces the overall cost of the formulation while maintaining or improving the functional performance of filament. The target properties for this particular embodiment of the high strength filament are: tensile strain: 10-50%; tensile strength: 50-100 MPa; Young's modulus: 500-1000 MPa; and Izod impact strength: 5-20 KJ/m$^2$.

TABLE 7

High Strength Filament Composition

| Component Category | Component | Percent Range (% m/m) |
| --- | --- | --- |
| Polyhydroxyalkanoate | Poly(3-hydroxybutyrate) | About 70% to about 80% |
| Toughening Agent | Polybutyrate adipate terephthalate | About 10% to about 20% |
| Plasticizer | Acetyl tri-n-butyl citrate | About 5% to about 20% |
| Filler | Calcium carbonate or Nanocrystalline cellulose | About 5% to about 20% or About 0.5% to about 10% |
| Nucleating Agent | Boron nitride | About 0.1% to about 1% |
| Coloring Agent | Organic pigment | About 0.01% to about 1% |
| Antioxidant | Pentaerythritol tetrakis(3-(3,5-di-tert-butyl-4-hydroxyphenyl)propionate | About 0.1% to about 1% |
| Adhesive | Epoxy-based adhesive | About 0.01% to about 2% |

Example 16: Wood Composite Filament

Wood composite formulations provide fine grainy surface finishes and textures similar to wood. Lignin or rice husk acts as a multipurpose filler, offering wood-like appearance, lowering the cost of formulation, providing dimensional stability and improving the crystallization behavior of the base polymer.

The properties projected for this composition are: tensile strain: 10-50%; tensile strength: 50-100 MPa; tensile modulus: 200-500 MPa; Young's modulus: 400-1000 MPa; and Izod impact strength: 5-20 KJ/m$^2$.

TABLE 8

Wood Composite Filament Composition

| Component Category | Component | Percent Range (% m/m) |
| --- | --- | --- |
| Polyhydroxyalkanoate | Poly(3-hydroxybutyrate) | About 60% to about 80% |
| Toughening Agent | Polybutyrate adipate terephthalate | About 10% to about 30% |
| Plasticizer | Acetyl tri-n-butyl citrate | About 5% to about 20% |
| Filler | Lignin or rice husk | About 5% to about 20% |
| Nucleating Agent | Boron nitride | About 0.1% to about 1% |
| Coloring Agent | Organic pigment | About 0.01% to about 1% |
| Antioxidant | Pentaerythritol tetrakis(3-(3,5-di-tert-butyl-4-hydroxyphenyl)propionate | About 0.1% to about 1% |
| Adhesive | Epoxy-based adhesive | About 0.01% to about 2% |

Example 17: Conductive Filament

Components printed using conductive filaments can be painted with variety of colors using conductive spray painting used widely in automotive industry. Conductive components generated by 3D printing can be used in cold weather conditions and can easily be defrosted by passing heat though the conducting component.

Conductive fillers such as carbon black provide conductivity at level as low as 0.01% by weight. Lower carbon black content does not affect most of the other properties of formulation, however, other conductive fillers including steel fibre and carbon nanotubes provides higher conductivity at the cost of ductility of the formulation. Toughening agents used in formulations of conducting filaments counteract brittleness caused by use of steel fibres and carbon nanotubes. Such formulations provide higher conductivity while maintaining other properties of the filaments.

The properties projected for this composition are: tensile strain: 10-50%; tensile strength: 50-100 MPa; tensile modulus: 50-100 MPa; Young's modulus: 500-1000 MPa; Izod impact strength: 5-20 KJ/m$^2$; and volume resistivity: 1×10$^4$ Ohm·cm.

TABLE 9

Conductive Filament Composition

| Component Category | Component | Percent Range (% m/m) |
|---|---|---|
| Polyhydroxyalkanoate | Poly(3-hydroxybutyrate) | About 60% to about 80% |
| Toughening Agent | Polybutyrate adipate terephthalate | About 10% to about 30% |
| Plasticizer | Acetyl tri-n-butyl citrate | About 0.5% to about 20% |
| Nucleating Agent | Boron nitride | About 0.1% to about 1% |
| Filler | Conductive carbon black | 0.01% to about 5% |
| Antioxidant | Pentaerythritol tetrakis(3-(3,5-di-tert-butyl-4-hydroxyphenyl)propionate | About 0.1% to about 1% |
| Adhesive | Epoxy-based adhesive | About 0.01% to about 2% |

In certain embodiments, the conductive carbon black may be replaced with about 1% to about 10% carbon nanotubes or about 1% to about 20% steel fibres.

Example 18: Glow-in-the-Dark Filament

There are a number of different uses of glow-in-the-dark filaments such as decorations and signage and/or instructions provided on highway signs and camping equipment.

The properties projected for this composition are: tensile strain: 10-50%; tensile strength: 50-100 MPa; tensile modulus: 50-100 MPa; Young's modulus: 500-1000 MPa; Izod impact strength: 5-20 KJ/m$^2$.

TABLE 10

Glow-in-the-Dark Filament Composition

| Component Category | Component | Percent Range (% m/m) |
|---|---|---|
| Polyhydroxyalkanoate | Poly(3-hydroxybutyrate) | About 50% to about 70% |
| Toughening Agent | Polybutyrate adipate terephthalate | About 30% to about 50% |
| Plasticizer | Acetyl tri-n-butyl citrate | About 10% to about 30% |
| Nucleating Agent | Boron nitride | About 0.1% to about 1% |
| Pigment | Organic pigment | 0.01% to about 1% |
| Phosphorescence compound | Zinc sulfide | About 0.01% to about 5% |
| Antioxidant | Pentaerythritol tetrakis(3-(3,5-di-tert-butyl-4-hydroxyphenyl)propionate | About 0.1% to about 1% |
| Adhesive | Epoxy-based adhesive | About 0.01% to about 2% |

In certain embodiments, strontium aluminate is used instead of zinc sulfide.

EQUIVALENTS AND SCOPE

Other than described herein, or unless otherwise expressly specified, all of the numerical ranges, amounts, values and percentages, such as those for amounts of materials, elemental contents, times and temperatures, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (i.e., end points may be used). When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

Any patent, publication, internet site, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

While this invention has been particularly shown and described with references to embodiments thereof, it will be understood by those skilled in the art that various changes in form and details may be made therein without departing from the scope of the invention encompassed by the appended claims.

The invention claimed is:

1. A multi-layer biodegradable film or coating, comprising one or more bioactive compounds or microorganisms for promoting growth or heath of a plant, the bioactive compounds or microorganisms contained within or between layers of the film, wherein each one of the layers comprises about 60% to about 75% (m/m) polyhydroxyalkanoate.

2. The multi-layer biodegradable film or coating of claim 1, wherein the bioactive compounds or microorganisms comprise any one of or a combination of: a metabolite, an anti-microbial or anti-fungal compound, enzyme, a carbohydrate, a nucleic acid, a protein, a live microorganism, a fertilizer, a plant growth hormone, a preservative, a pesticide or an herbicide.

3. The multi-layer biodegradable film or coating of claim 2 wherein the plant growth hormone comprises any one of or a combination of a synthetic hormone, an auxin, a gibberellin, a cytokinin, a brassinosteroid, abscisic acid and ethylene.

4. The multi-layer biodegradable film or coating of claim 1, wherein at least one layer of the two or more layers has a composition configured to undergo controlled, timed biodegradation at a different rate than the rates of biodegradation of remaining layers of the two or more layers.

5. The multi-layer biodegradable film or coating of claim 1 comprising three or more layers of the biodegradable film having at least a first bioactive compound or microorganism in or between a first layer of the biodegradable film and a second layer of the biodegradable film and at least a second bioactive compound or microorganism in or between the second layer of the biodegradable film and a third layer of the biodegradable film or at least a first bioactive compound or organism located in or within one of the three or more layers and at least a second bioactive compound or organism located in or between another of the three or more layers.

6. The multi-layer biodegradable film or coating of claim 5, wherein the first bioactive compound is a plant hormone promoting seed germination and the second bioactive compound is a plant hormone which promotes stem elongation, leaf growth, fruiting, injury repair, water uptake or protection against extreme temperatures or wherein the second bioactive compound is an herbicide or an insecticide.

7. The multi-layer film of claim 5, wherein the first layer has a composition different from the second and third layers, the second layer has a composition different than the first and third layers and the third layer has a composition different than the first and second layers.

8. The multi-layer biodegradable film of claim 5, wherein at least one of the three layers of the biodegradable film degrades at a faster rate than the remaining two layers to provide different bioactive compounds for different growth needs.

9. The multi-layer biodegradable film or coating of claim 1, wherein degradation of one or more of the layers is initiated by an artificial stimulus or a natural environmental stimulus.

10. The multi-layer biodegradable film or coating of claim 9, wherein the artificial stimulus is a change in temperature, administration of an electrical current or irradiation with light.

11. The multi-layer biodegradable film or coating of claim 9, wherein the natural environmental stimulus is precipitation, sunlight, pH, nutrient concentration or other natural trigger.

12. The multi-layer biodegradable film or coating of claim 11, wherein at least one of the layers comprises about 0.5% to about 30% (m/m) of a filler comprising charcoal, a carbon nanotube, a carbon fiber, a steel fiber, graphene graphite, carbon black, algae, cellulose, nano crystalline cellulose, biochar clay or any combination thereof.

13. The multi-layer biodegradable film or coating of claim 12, wherein the filler conducts electricity and/or light.

14. The multi-layer biodegradable film or coating of claim 1 wherein one or more of the bioactive compounds are encased in hydrogel or a thermoprotectant to protect the bioactive compounds against degradation during manufacture.

15. The multi-layer biodegradable film or coating of claim 1, wherein a first bioactive compound of the one or more bioactive compounds is a microorganism located within or adjacent to a first layer of the film, the microorganism capable of metabolizing polyhydroxyalkanoate released from the first layer.

16. The multi-layer biodegradable film or coating of claim 15, wherein the microorganism promotes degradation of a second layer of the film and wherein degradation of the second layer releases a second bioactive compound which enhances plant growth.

17. The multi-layer biodegradable film or coating of claim 1, wherein a first bioactive compound released from at least one of the layers triggers activity of a second bioactive compound from a previously degraded layer.

18. The multi-layer biodegradable film or coating of claim 1, wherein at least one of the layers has micro- or nano-pores or channels provided to allow uptake or release of one or more nutrients or one or more additional bioactive compounds, wherein the micro- or nano-pores or channels are activated by environmental conditions and/or biodegradation of the layers to expose the micro- or nano-pores or channels and allow transport of the nutrients or additional bioactive compounds.

19. A method for promoting growth of a tree or plant, the method comprising the steps of:
  a) at least partially wrapping the tree or plant or covering a seed of the plant with the multi-layer biodegradable film or coating of claim 1, wherein the film includes a filler that conducts electricity and/or light, and
  b) providing an electric current and/or light to the film, thereby promoting the release of the bioactive compounds or microorganisms.

20. The method of claim 19, wherein the electricity and/or light breaks down one or more of the layers, thereby allowing the bioactive compounds or microorganisms to be released from the multi-layer film.

* * * * *